US012773494B2

(12) United States Patent
Jeon et al.

(10) Patent No.: US 12,773,494 B2
(45) Date of Patent: Oct. 27, 2026

(54) LIQUID MEDICINE INJECTION DEVICE

(71) Applicant: EOFLOW CO., LTD., Seongnam-si (KR)

(72) Inventors: Ho Min Jeon, Yongin-si (KR); Yongjoon Han, Seoul (KR)

(73) Assignee: EOFLOW CO., LTD., Seongnam-si (KR)

( * ) Notice: Subject to any disclaimer, the term of this patent is extended or adjusted under 35 U.S.C. 154(b) by 1024 days.

(21) Appl. No.: 17/757,184

(22) PCT Filed: Dec. 11, 2020

(86) PCT No.: PCT/KR2020/018122
§ 371 (c)(1),
(2) Date: Jun. 10, 2022

(87) PCT Pub. No.: WO2021/118282
PCT Pub. Date: Jun. 17, 2021

(65) Prior Publication Data

US 2023/0011504 A1 Jan. 12, 2023

(30) Foreign Application Priority Data

Dec. 11, 2019 (KR) ........................ 10-2019-0165013
Dec. 17, 2019 (KR) ........................ 10-2019-0169186

(51) Int. Cl.
*A61M 5/142* (2006.01)
*A61M 5/172* (2006.01)

(52) U.S. Cl.
CPC ...... *A61M 5/14248* (2013.01); *A61M 5/1723* (2013.01); *A61M 2005/14252* (2013.01)

(58) Field of Classification Search
CPC ...... A61M 5/1723; A61M 2005/14252; A61M 5/14248; A61M 2205/3303; A61B 5/14532; A61B 5/4839; A61B 2560/0443
See application file for complete search history.

(56) References Cited

U.S. PATENT DOCUMENTS 10,413,665 B2 9/2019 Rioux et al.
2002/0169439 A1 11/2002 Flaherty
(Continued)

FOREIGN PATENT DOCUMENTS

EP 3415184 A1 12/2018
JP 2010-508123 A 3/2010
(Continued)

OTHER PUBLICATIONS

International Search Report issued for International Patent Application No. PCT/KR2020/018122, dated Jun. 8, 2021 in 13 pages including English translation.
(Continued)

*Primary Examiner* — Theodore J Stigell
(74) *Attorney, Agent, or Firm* — Knobbe, Martens, Olson & Bear, LLP

(57) ABSTRACT

The present disclosure relates to a liquid medicine injection device including a patch portion to which a sensor portion configured to measure blood glucose is detachable and in which an injection portion configured to inject a liquid medicine into the body of a user is installed, and a stamping portion on which the patch portion is mounted and including a first needle connectable to the sensor portion, wherein the stamping portion transmits power to the patch portion so that the first needle and a second needle, which is connected to the injection portion, are together inserted into the skin of the user, and the sensor portion and the injection portion are installed in a single device so that the convenience of use is improved when the liquid medicine injection device is attached to the skin of the user.

11 Claims, 21 Drawing Sheets

(56) References Cited

U.S. PATENT DOCUMENTS

| | | | | |
|---|---|---|---|---|
| 2006/0253085 | A1 | 11/2006 | Geismar et al. | |
| 2012/0184909 | A1 * | 7/2012 | Gyrn | A61B 5/6849 604/257 |
| 2015/0141776 | A1 * | 5/2015 | Hadvary | A61B 5/14503 604/173 |
| 2021/0316066 | A1 * | 10/2021 | Kim | A61M 5/158 |

FOREIGN PATENT DOCUMENTS

| | | | |
|---|---|---|---|
| JP | 2013-509269 | A | 3/2013 |
| KR | 10-1998-0079154 | A | 11/1998 |
| KR | 10-1290983 | B1 | 7/2008 |
| KR | 10-2015-0005604 | A | 1/2015 |
| KR | 10-2015-0036869 | A | 4/2015 |
| KR | 10-2018-0055389 | A | 5/2018 |
| WO | WO 2009/060432 | A1 | 5/2009 |
| WO | WO 2011/015659 | A1 | 2/2011 |

OTHER PUBLICATIONS

Written Opinion issued for International Patent Application No. PCT/KR2020/018122, dated Jun. 8, 2021 in 4 pages.

Extended European Search Report dated Dec. 13, 2022 in Application No. 20899359.2, 8 pages.

* cited by examiner

LIQUID MEDICINE INJECTION DEVICE

CROSS-REFERENCE TO RELATED APPLICATIONS

This application is the U.S. National Phase under 35. U.S.C. § 371 of International Application PCT/KR2020/018122, filed Dec. 11, 2020, which claims priority to Korean Patent Application No. 10-2019-01650133, filed Dec. 11, 2019, and Korean Patent Application No. 10-2019-0169186, filed Dec. 17, 2019. The disclosure of each of the above-described applications is hereby incorporated by reference in its entirety.

TECHNICAL FIELD

The present disclosure relates to a liquid medicine injection device.

DESCRIPTION OF THE RELATED ART

Generally, liquid medicine injection devices such as insulin injection devices are used to inject liquid medicines into the bodies of patients. Such liquid medicine injection devices are used by professional medical staff such as nurses or doctors but are mostly used by ordinary persons such as caretakers or patients themselves.

In the case of diabetic patients, particularly pediatric diabetic patients, it is necessary to inject liquid medicines such as insulin into a human body at regular intervals. A patch-type liquid medicine injection device that may be used by being attached to a human body for a predetermined period of time has been developed, and such a liquid medicine injection device may be used while being attached as a patch type to the abdomen or waist of a patient for a predetermined period of time.

In order to increase the effect of the injection of a liquid medicine, the liquid medicine injection device needs to be controlled to precisely inject the liquid medicine into the body of a patient, and accordingly, it is important to precisely inject a small amount of the liquid medicine through a small-sized liquid medicine injection device.

Conventionally, there is a problem in that the convenience of use is reduced, for example, a sensor for measuring blood glucose of a user and an injection device for injecting a liquid medicine such as insulin into the body of the user must be separately provided, and the user has to dispose each of the sensor and the injection device on the skin of the user by bringing them into contact with the skin of the user.

Further, there is a problem in that when a situation occurs in which the liquid medicine injection device does not operate properly occurs, and the user does not recognize this situation, the liquid medicine is not injected normally into the body of the user, and the user is not able to respond urgently to such an emergency situation unless the user directly checks the liquid medicine injection device.

SUMMARY OF CERTAIN INVENTIVE ASPECTS

The present disclosure has been made in an effort to resolve the above-described problems, and provides a liquid medicine injection device capable of improving the convenience of use when being attached to the skin of a user by installing a sensor portion and an injection portion in a single device.

The present disclosure also provides a liquid medicine injection device capable of improving the convenience of use by allowing a first needle connected to a sensor portion and a second needle connected to an injection portion to be momentarily inserted together into and then separated from the skin of a user while a stamping portion transmits power to a patch portion with a simple operation of pushing the stamping portion by the user.

The present disclosure also provides a liquid medicine injection device capable of promptly delivering an emergency situation in which an injection portion does not operate normally to a user, thereby responding to the emergency situation.

According to one embodiment of the present disclosure, there is provided a liquid medicine injection device including a patch portion to which a sensor portion configured to measure blood glucose is detachable and in which an injection portion configured to inject a liquid medicine into the body of a user is installed, and a stamping portion on which the patch portion is mounted and including a first needle connectable to the sensor portion, wherein the stamping portion transmits power to the patch portion so that the first needle and a second needle, which is connected to the injection portion, are together inserted into the skin of the user.

In the present disclosure, the stamping portion may include a first body allowed to be gripped by the user, a second body that is relatively movable inside the first body, and a patch holder portion that is connected to the second body, disposed to be spaced apart from the first body by a predetermined separation distance, and in which the patch portion is mounted.

In the present disclosure, the stamping portion may further include a power transmission portion configured to connect the first body and the patch holder portion and transmit power to the injection portion to separate the second needle connected to the injection portion from the skin of the user.

In the present disclosure, the power transmission portion may rotate in a clockwise direction or a counterclockwise direction and transmits rotational power to the injection portion.

In the present disclosure, the injection portion may include an injection cover connected to the power transmission portion, an injection housing coupled to the injection cover and having a hollow interior, a tube portion installed in the injection housing and having a hollow interior, and a second needle holder portion which is disposed to be movable inside the injection housing and in which the second needle insertable into the tube portion is installed.

In the present disclosure, the injection housing and the second needle holder portion may share a rotation central axis and may be relatively rotatable with respect to each other.

In the present disclosure, the injection portion may further include a sealing member coupled along an outer circumferential surface of the injection cover.

In the present disclosure, the sealing member may be formed in a ring shape.

In the present disclosure, the power transmission portion may include a power transmission shaft formed to extend in a longitudinal direction and configured to rotate about a longitudinal central axis in the clockwise direction or the counterclockwise direction, and a shaft holder portion that is connected to the power transmission shaft and movable on the power transmission shaft.

In the present disclosure, a movement control portion disposed between the shaft holder portion and the second body and configured to control a movement of the shaft holder portion may be formed in the patch holder portion.

In the present disclosure, the liquid medicine injection device may further include a first needle holder portion in which the first needle is installed, and which is relatively movable with respect to the patch holder portion.

In the present disclosure, the first needle holder portion may include a first needle holder body to which the first needle is positionally fixed, and an elastic member coupled to each of the first needle holder body and the patch holder portion and configured to elastically support the first needle holder body in a direction away from the patch holder portion.

In the present disclosure, a movement control portion disposed between the first needle holder portion and the second body and configured to control a movement of the first needle holder portion may be formed in the patch holder portion.

In the present disclosure, a sensor mounting groove on which the sensor portion is mountable may be formed in the shape of a groove in the patch portion, and the liquid medicine injection device may further include a sensor mounting portion that is couplable to the stamping portion, and has one surface facing the patch portion in which the sensor mounting groove is formed and on which the sensor portion is disposed to protrude.

In the present disclosure, the sensor portion may include a sensor module including a sensor needle disposed inside the first needle, and a sensor cover coupled to the sensor module and configured to cover the sensor module.

According to one embodiment of the present disclosure, there is provided a liquid medicine injection device including an injection body configured to inject a liquid medicine into the body of a user, a driving detection portion that is electrically connected to the injection body and configured to detect information on a driving state of the injection body, an alarm body configured to transmit information for detecting an abnormal symptom of the driving state of the injection body generated on the basis of the information on the driving state of the injection body detected by the driving detection portion to a user, and a control portion that is electrically connected to the injection body, the driving detection portion, and the alarm body and configured to control the driving of each of the injection body, the driving detection portion, and the alarm body.

In the present disclosure, the injection body may include a needle portion capable of penetrating into the body of the user and a driving portion configured to transmit power to the needle portion.

In the present disclosure, the driving detection portion may include a driving sensor that is electrically connected to the driving portion and configured to sense a driving state of the driving portion, and a danger signal generating portion configured to generate a danger signal on the basis of information on the driving state of the driving portion sensed by the driving sensor.

In the present disclosure, the liquid medicine injection device may include an injection portion including the injection body and the driving detection portion, and an alarm portion including the alarm body, and the control portion may include a first control portion that is electrically connected to the injection body and the driving detection portion and provided in the injection portion, and a second control portion that is electrically connected to the alarm body and located in the alarm portion.

In the present disclosure, the injection portion and the alarm portion are communicatable with each other.

In the present disclosure, the alarm body may include a stimulation transmission portion configured to receive an electrical signal from the second control portion and apply a stimulation to the user.

Other aspects, features, and advantages other than the above-described features will be apparent from the following drawings, claims, and detailed descriptions of the disclosure.

In a liquid medicine injection device according to the embodiments of the present disclosure, a stamping portion can transmit power to a patch portion due to the simple operation of pushing the stamping portion by a user, so that a first needle and a second needle, which is connected to an injection portion, are momentarily inserted together into and separated from the skin of the user, so that the convenience of use can be improved.

Further, a rotation guide groove formed in a power transmission shaft is formed at a predetermined angle with respect to a longitudinal direction of the power transmission shaft in a predetermined section along the longitudinal direction of the power transmission shaft, so that a linear movement of a shaft holder body can be converted into a rotational movement of the power transmission shaft.

Further, since a protrusion formed on a power transmission shaft is inserted into an insertion groove formed in an injection cover, as the power transmission shaft rotates, the injection cover is rotated together with the power transmission shaft, so that a second needle holder portion on which a second needle is installed can move within the injection housing, and the second needle can be separated from the skin of a user.

Further, an outer circumferential surface of a first needle holder body comes into surface contact with a movement control portion, which is formed on a patch holder portion, to be inclined, so that the first needle holder body can be stably spaced apart from the patch holder portion by an elastic restoring force of an elastic member.

Further, an outer circumferential surface of a shaft holder body comes into surface contact with a movement control portion, which is formed on a patch holder portion, to be inclined, so that the shaft holder body can be stably spaced apart from the patch holder portion by an elastic restoring force of an elastic member.

Further, in a situation in which an injection portion does not operate normally, this situation can be promptly delivered to a user so that an emergency situation can be responded.

Further, an alarm body transmits information for detecting an abnormal symptom of a driving state of an injection body, which is generated on the basis of information on the driving state of the injection body, to a user, so that the user can immediately detect the abnormal symptom of the driving state.

Further, an alarm body is located in an alarm portion while being in contact with the skin of a user such as the wrist, and not exposed to the outside as the user wears the alarm portion, so that the third party except for the user may not recognize a stimulation, which is transmitted to the user when an abnormal symptom of a driving state of an injection portion is detected, and only the user can recognize the stimulation.

Of course, the scope of the present disclosure is not limited by these effects.

DETAILED DESCRIPTION OF CERTAIN ILLUSTRATIVE EMBODIMENTS

Figure 1:
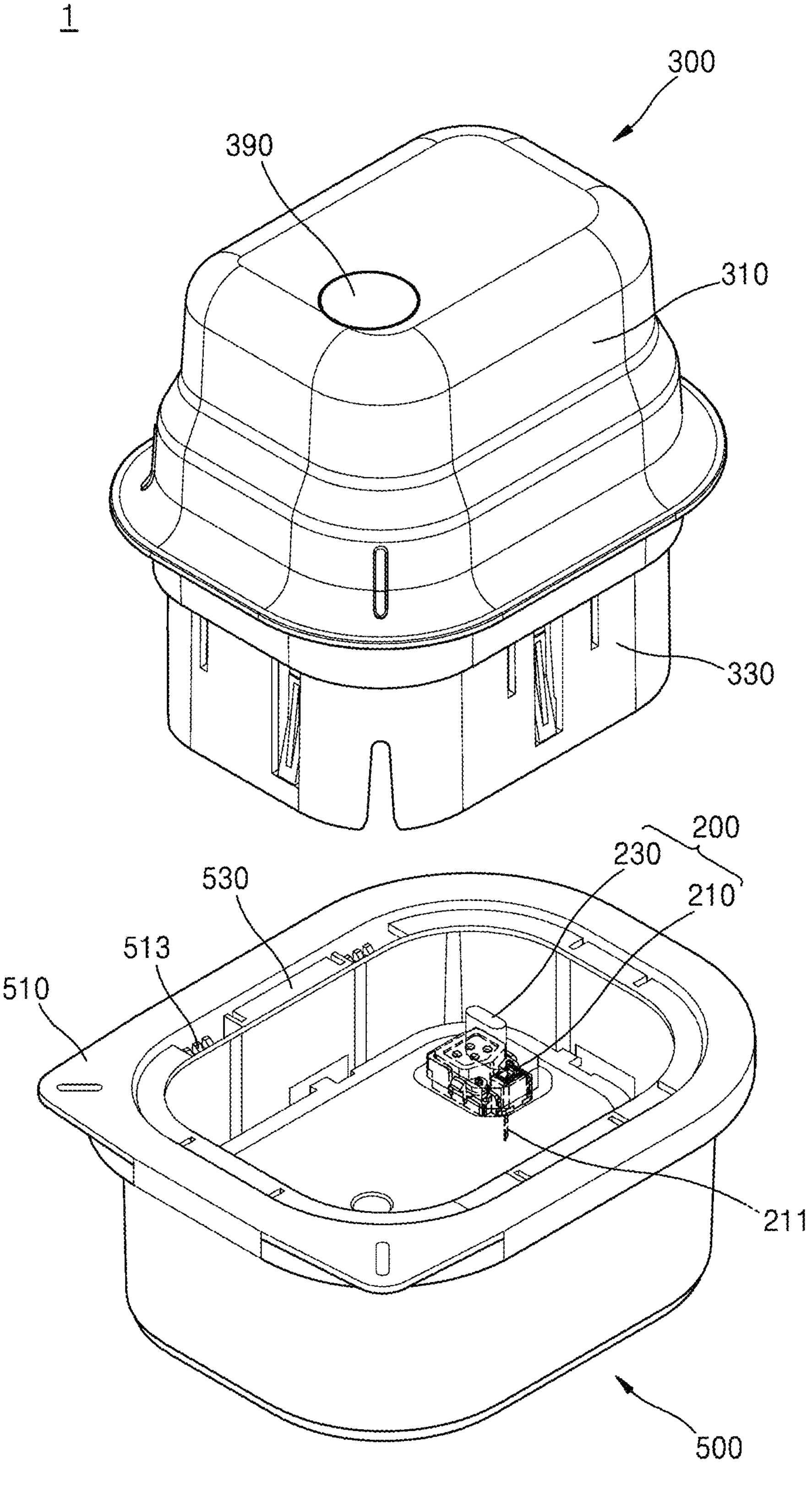
FIG. 1 is a perspective view illustrating a liquid medicine injection device according to one embodiment of the present disclosure.

While the present disclosure is susceptible to various modifications and alternative forms, specific embodiments thereof are shown by way of example in the drawings and will herein be described in detail. The effects and features of the present disclosure and the accompanying methods thereof will become apparent from the following description of the embodiments, taken in conjunction with the accompanying drawings. However, the present disclosure is not limited to the embodiments described below, and may be embodied in various modes.

Hereinafter, the embodiments of the present disclosure will be described below in detail with reference to the accompanying drawings, and when the embodiments of the present disclosure are described with reference to the drawings, the same or corresponding components are given the same reference numerals, and repetitive descriptions thereof will be omitted.

It will be understood that although the terms "first," "second," etc. may be used herein to describe various elements, these elements should not be limited by these terms. These elements are only used to distinguish one element from another.

In the following embodiments, singular forms are intended to include plural forms as well, unless the context clearly indicates otherwise.

In the following embodiments, the terms such as "including," "having," and "comprising" are intended to indicate the existence of features or components disclosed in the specification, and are not intended to preclude the possibility that one or more other features or components may be added.

In the following embodiments, when it is stated that a portion such as a film, region, component, and the like is above or on another portion, the portion may not only be directly on the other portion but may also be on the other portion with still another film, area, component, and the like interposed therebetween.

In the drawings, for convenience of description, sizes of components may be exaggerated or reduced. For example, since the size and thickness of each component illustrated in the drawing are arbitrarily shown for convenience of description, the present disclosure is not necessarily limited to those illustrated in the drawing.

When a certain embodiment may be implemented differently, a specific process sequence may be performed differently from the described order. For example, two consecutively described processes may be performed substantially at the same time or performed in an order opposite to the described order.

In the following embodiments, when it is stated that films, regions, components, or the like are connected to each other, the films, regions, and components may not only be directly connected to each other but may also be indirectly connected to another film, region, and component interposed therebetween. For example, in the specification, when it is stated that films, regions, components, or the like are electrically connected, the films, regions, components, or the like may not only be directly connected electrically to each other but may also be indirectly connected to each other electrically with another film, region, component, or the like interposed therebetween.

Figure 2:
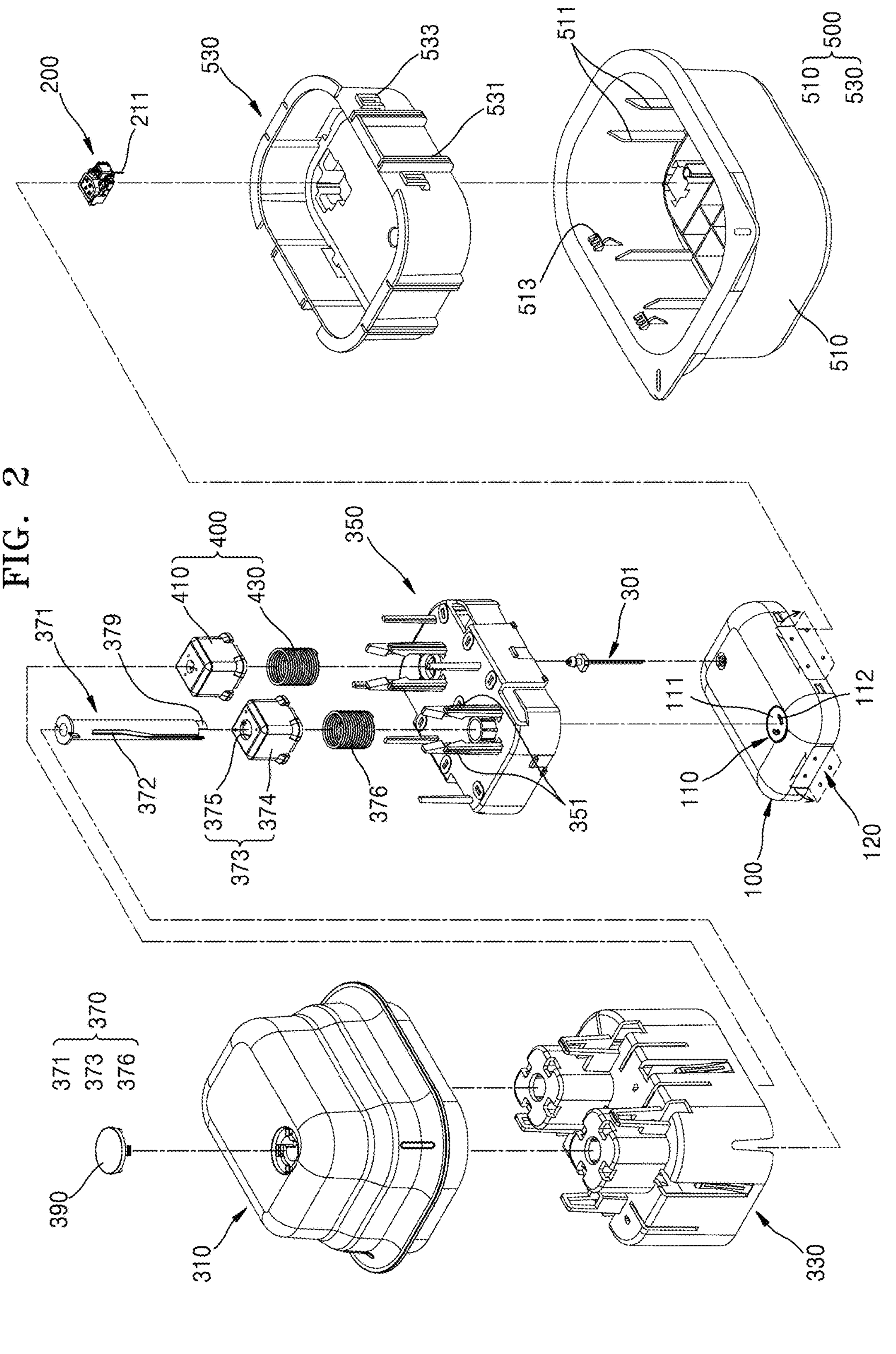
FIG. 2 is an exploded view illustrating the liquid medicine injection device according to one embodiment of the present disclosure.
Figure 3:
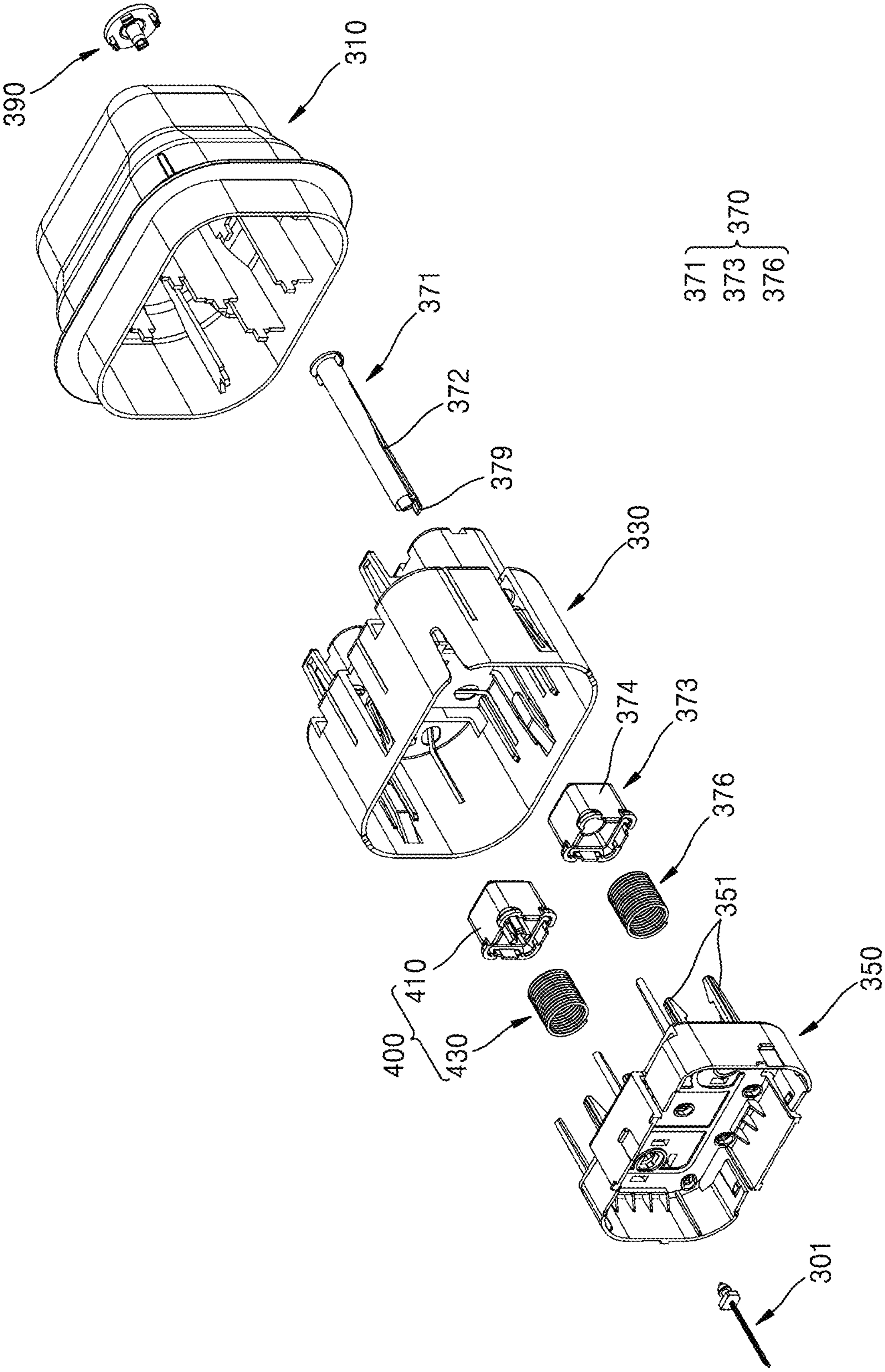
FIG. 3 is an exploded view illustrating a stamping portion according to one embodiment of the present disclosure.
Figure 4:
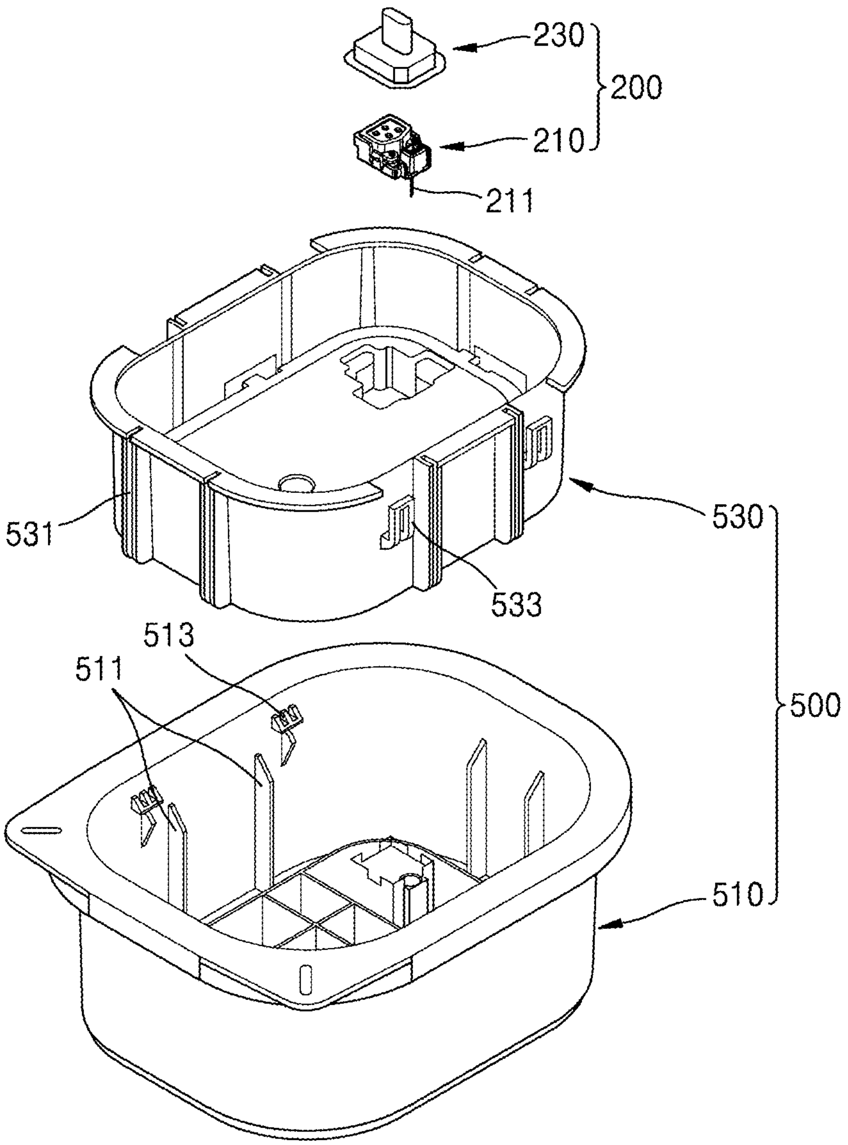
FIG. 4 is an exploded view illustrating a sensor mounting portion according to one embodiment of the present disclosure.
Figure 5:
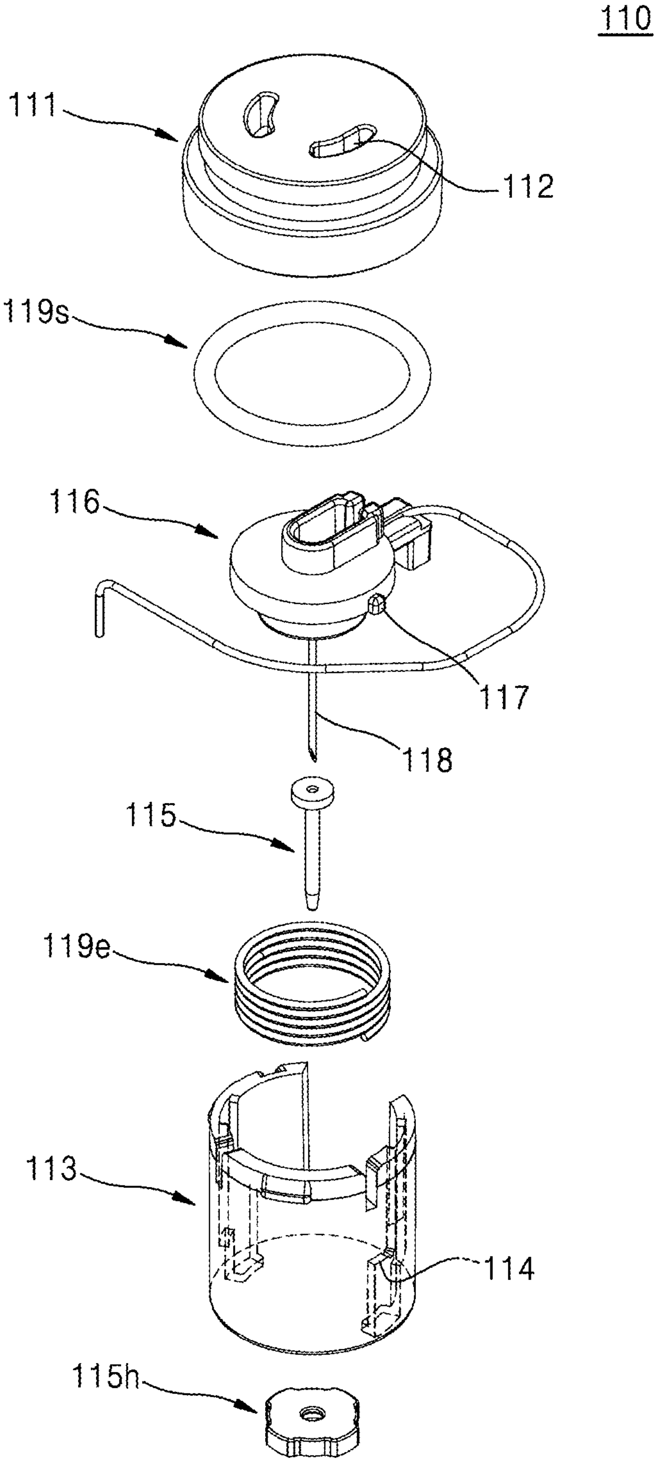
FIG. 5 is an exploded view illustrating an injection portion according to one embodiment of the present disclosure.
Figure 6A:
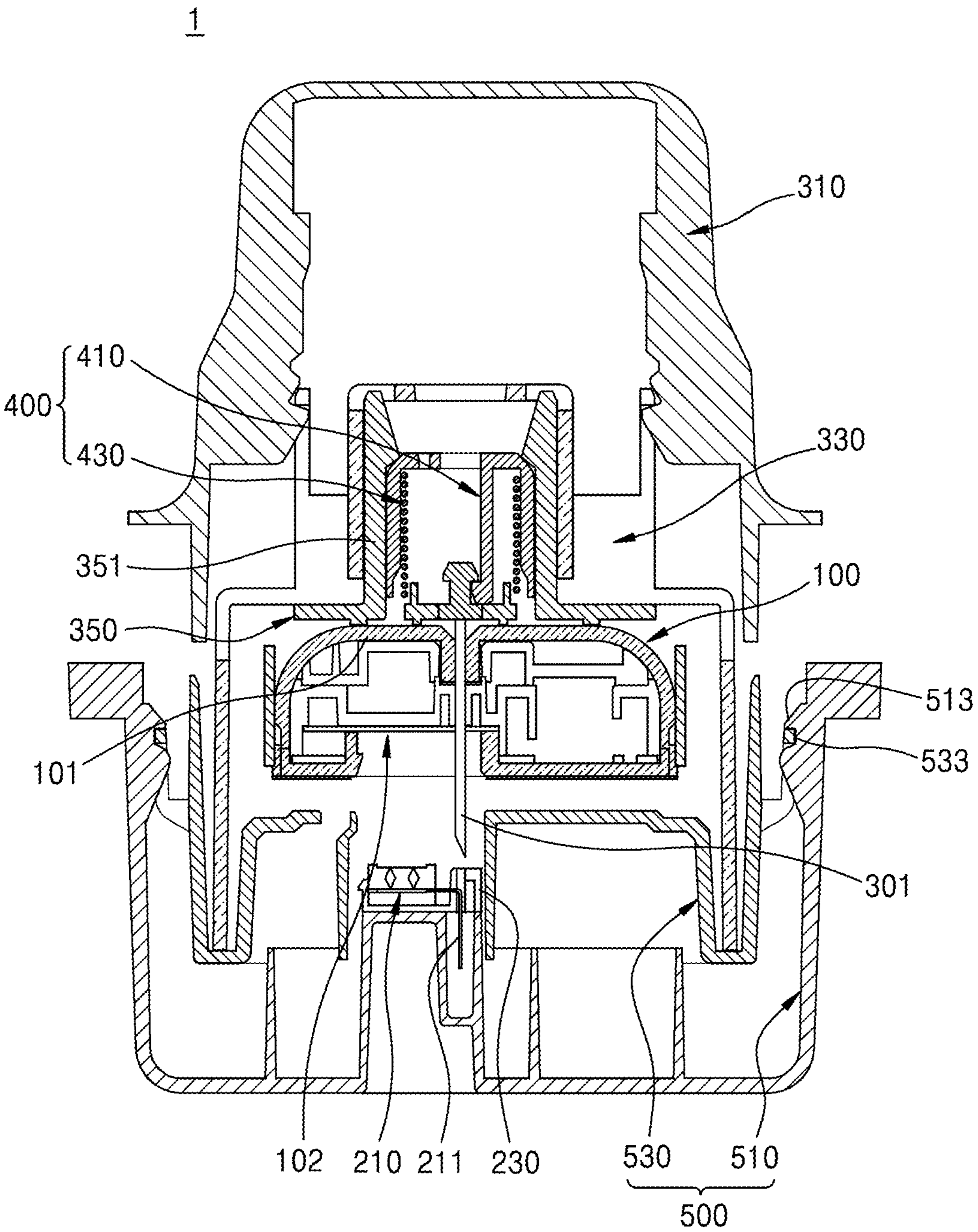
FIGS. 6A and 6B are side cross-sectional views illustrating a process of mounting a sensor portion to a patch portion according to one embodiment of the present disclosure.
Figure 6B:
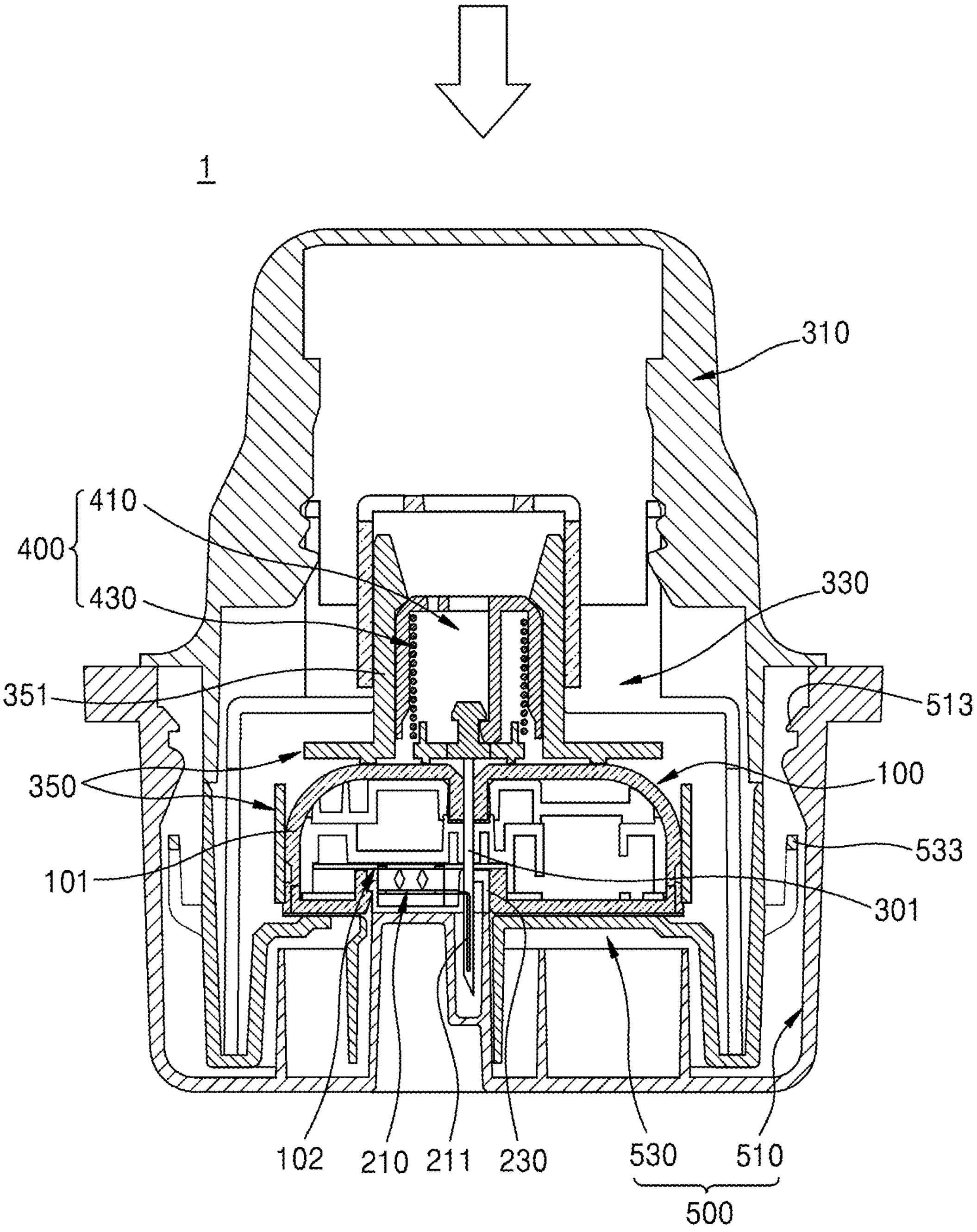
Figure 6C:
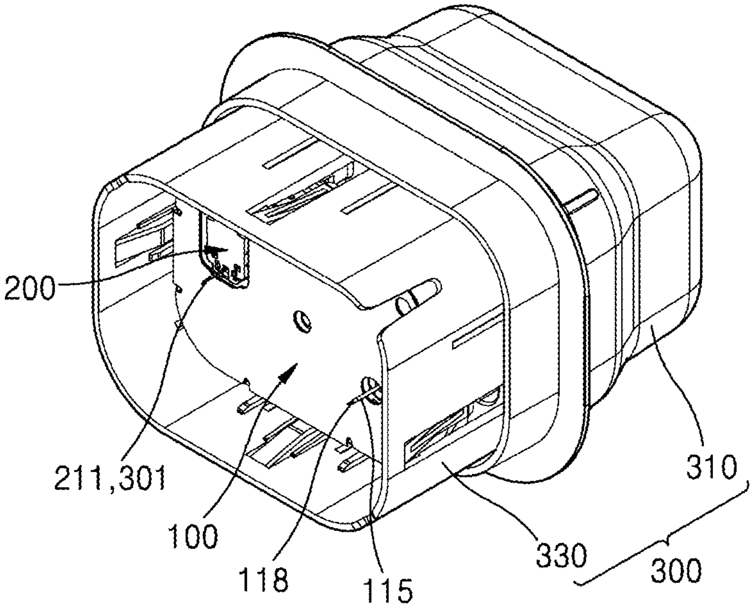
FIG. 6C is a bottom perspective view illustrating a state in which the patch portion is mounted to the stamping portion according to one embodiment of the present disclosure.
Figure 7A:
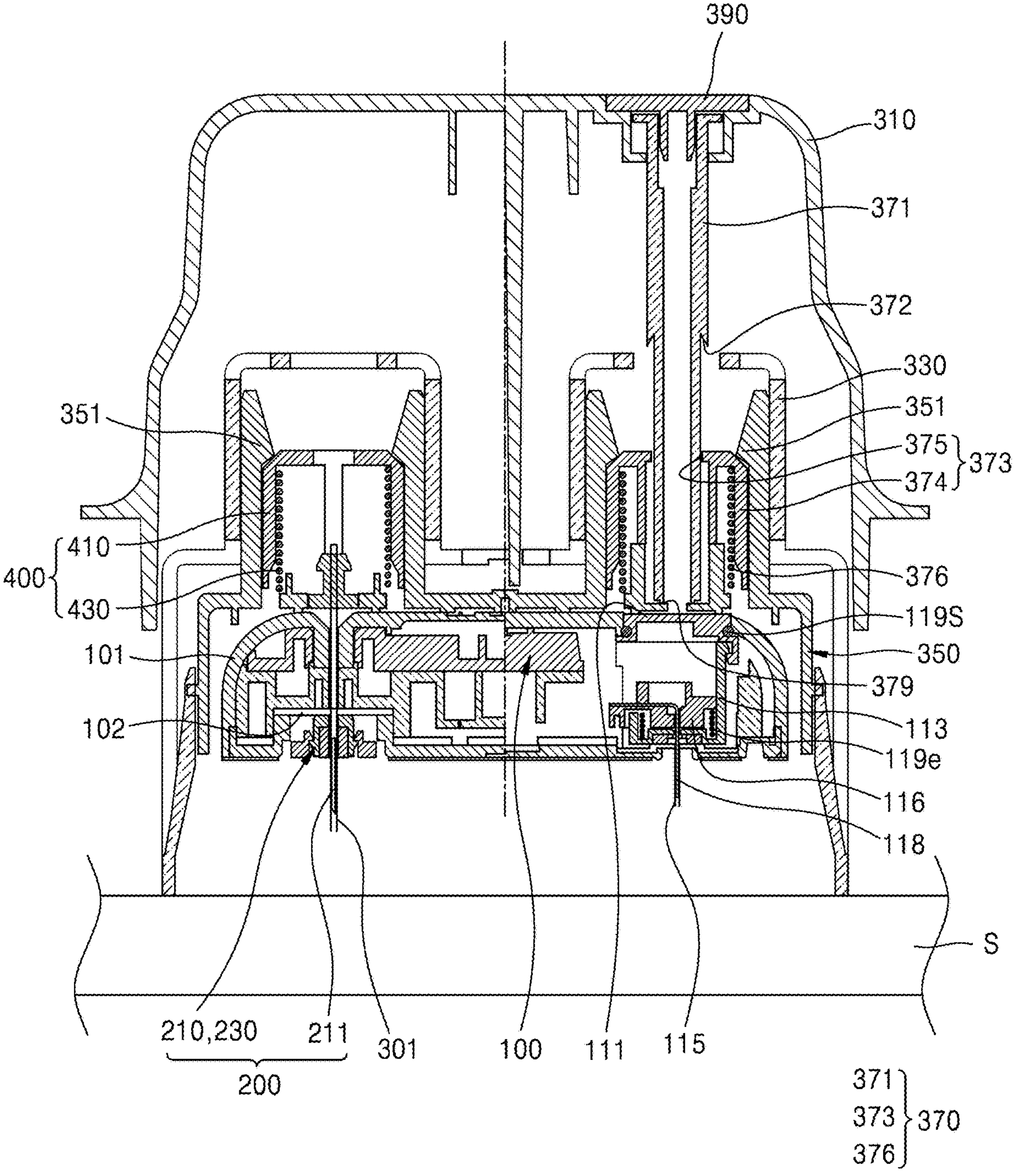
FIGS. 7A to 7C are cross-sectional views illustrating a state in which the sensor portion and the injection portion are brought into contact with a user according to one embodiment of the present disclosure.
Figure 7B:
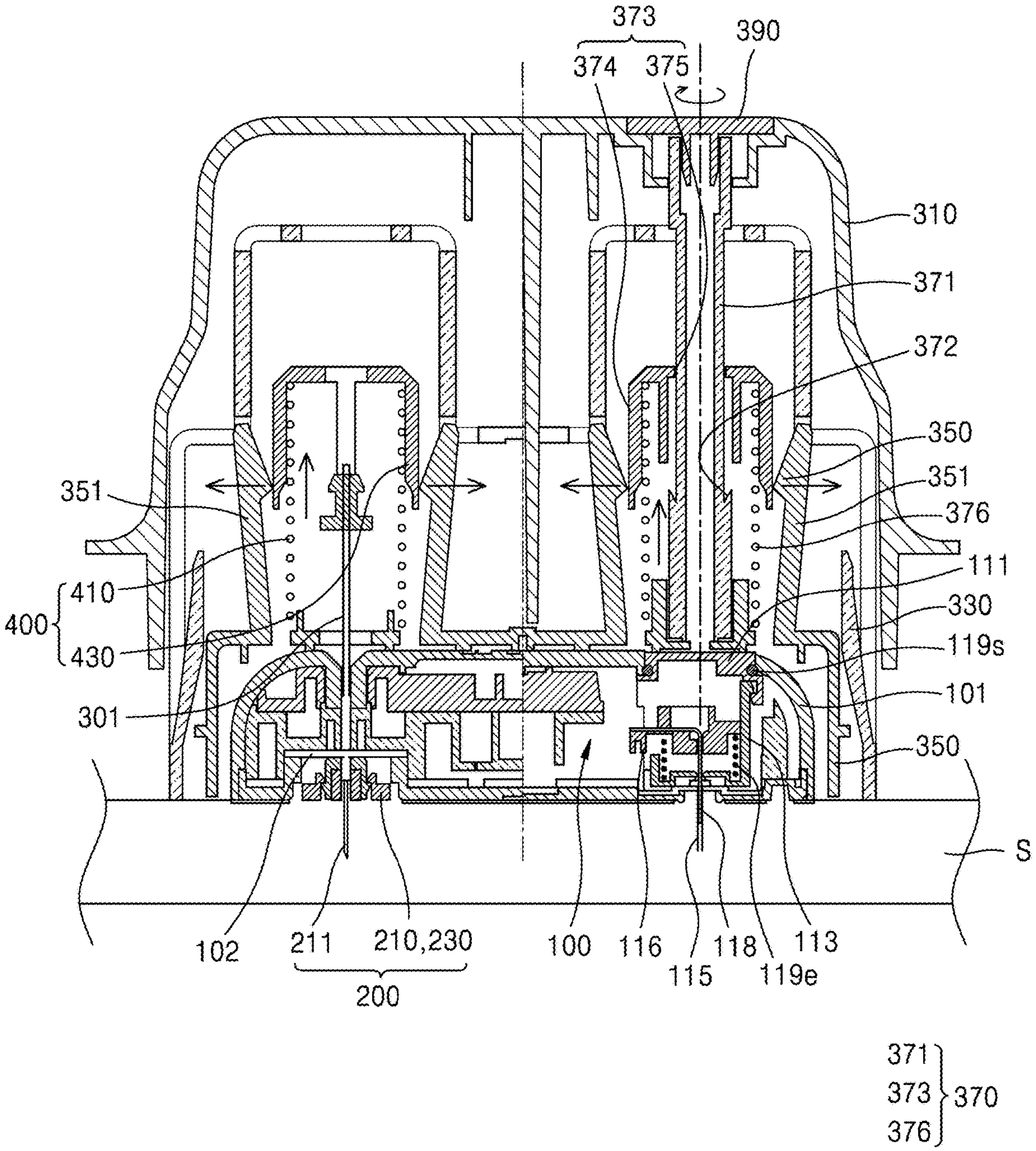
Figure 7C:
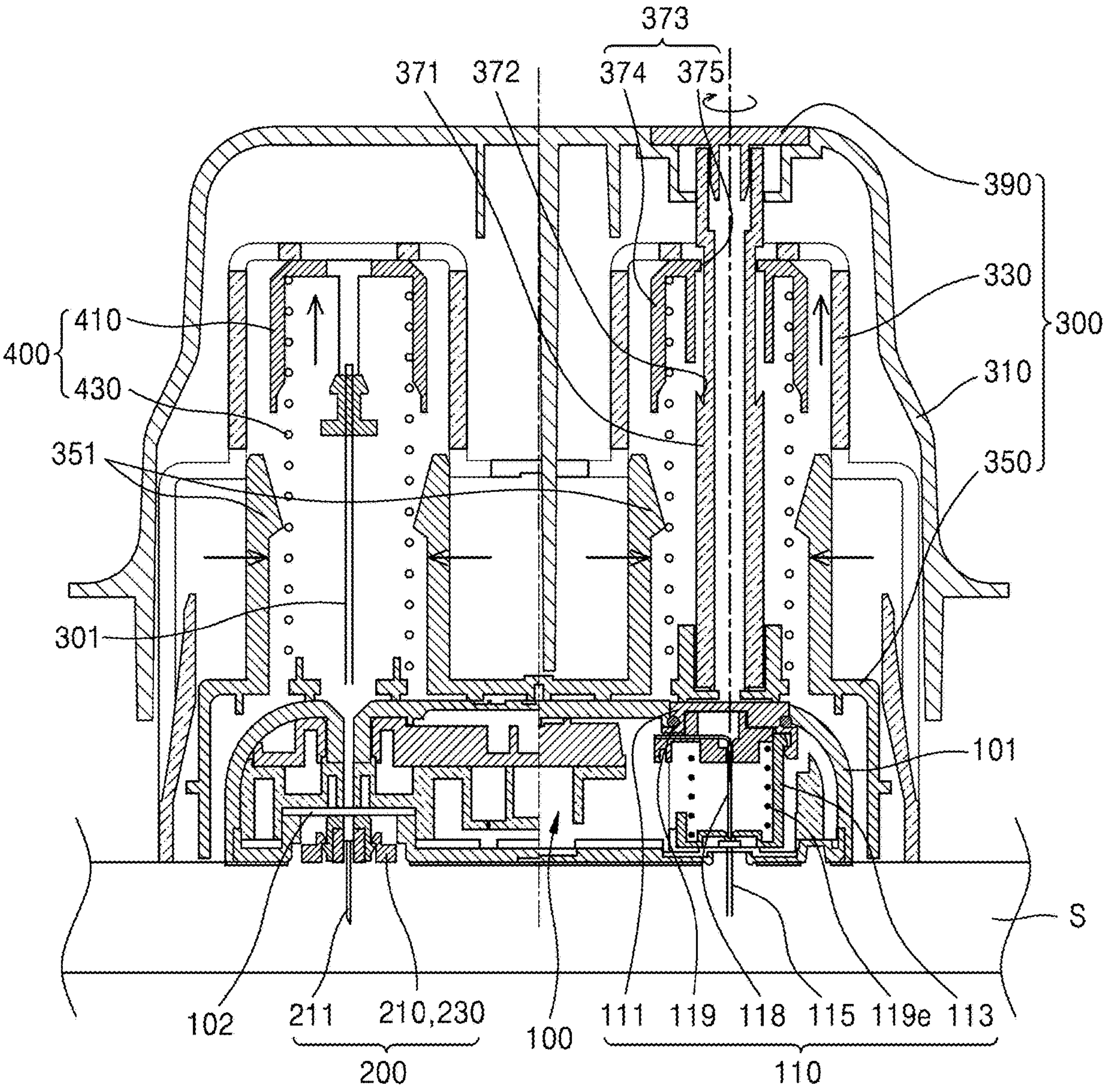
Figure 8A:
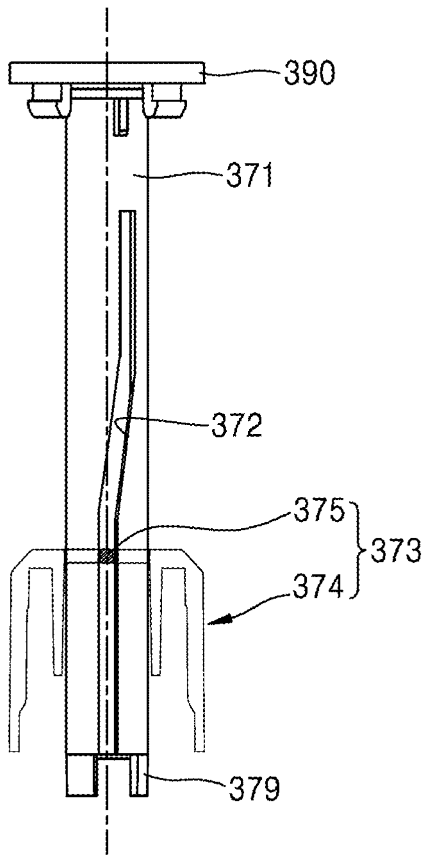
FIGS. 8A and 8B are conceptual diagrams illustrating a state in which a power transmission shaft rotates according to one embodiment of the present disclosure.
Figure 8B:
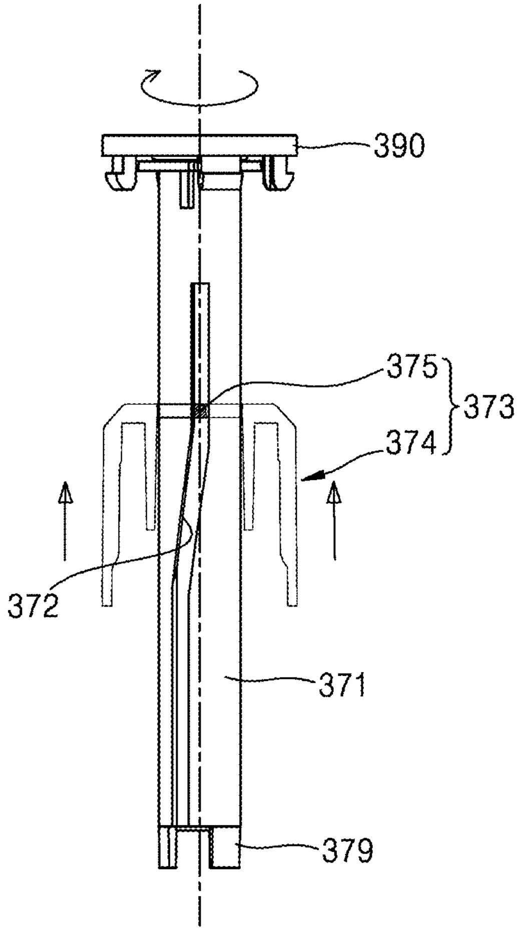
Figure 9A:
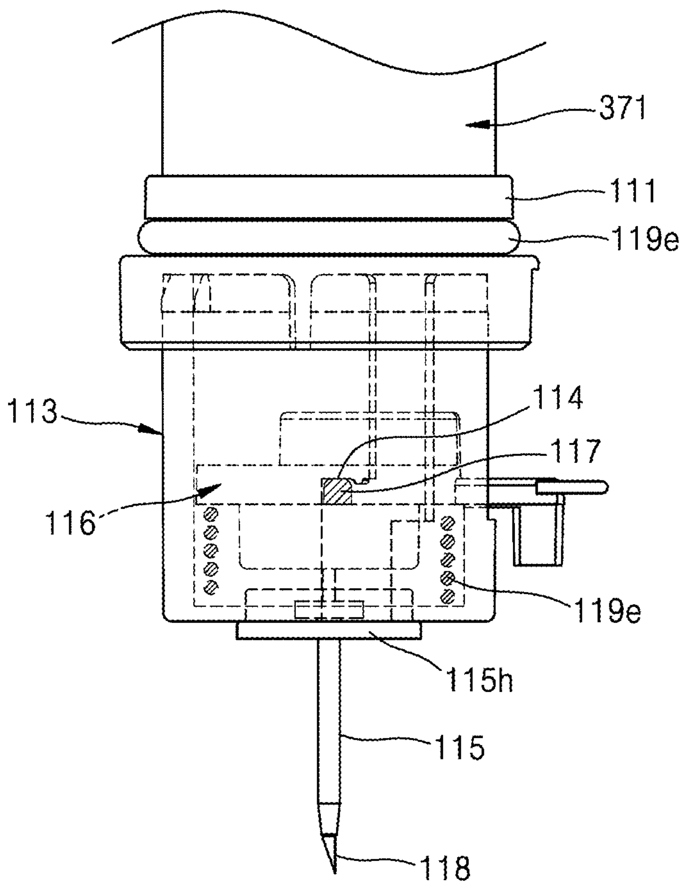
FIGS. 9A and 9B are conceptual diagrams illustrating a state in which a second needle moves in the injection portion according to one embodiment of the present disclosure.
Figure 9B:
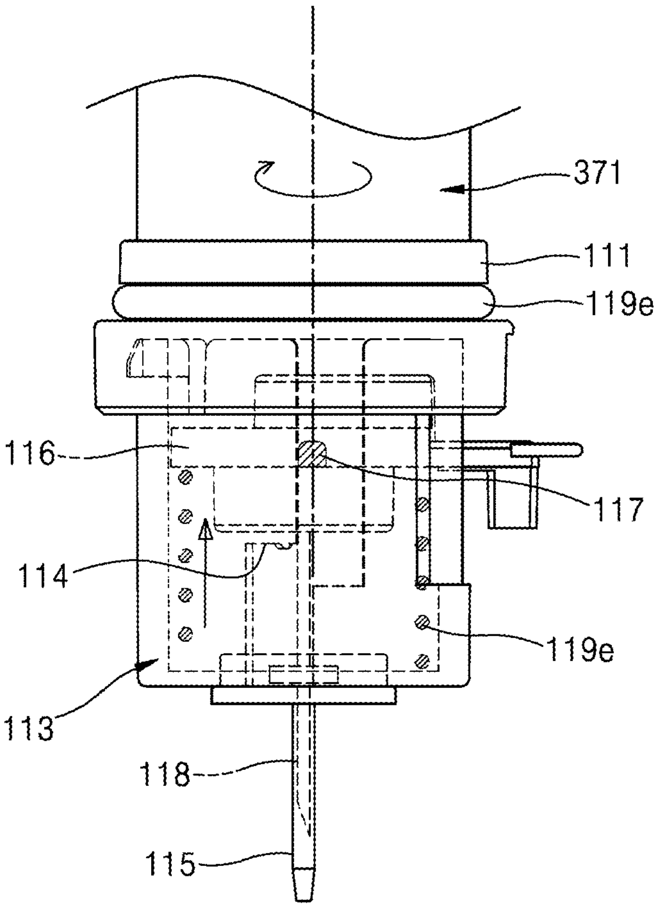

FIG. 1 is a perspective view illustrating a liquid medicine injection device according to one embodiment of the present disclosure. FIG. 2 is an exploded view illustrating the liquid medicine injection device according to one embodiment of the present disclosure. FIG. 3 is an exploded view illustrating a stamping portion according to one embodiment of the present disclosure. FIG. 4 is an exploded view illustrating a sensor mounting portion according to one embodiment of the present disclosure. FIG. 5 is an exploded view illustrating an injection portion according to one embodiment of the present disclosure. FIGS. 6A and 6B are side cross-sectional views illustrating a process of mounting a sensor portion to a patch portion according to one embodiment of the present disclosure. FIG. 6C is a bottom perspective view illustrating a state in which the patch portion is mounted to the stamping portion according to one embodiment of the present disclosure. FIGS. 7A to 7C are cross-sectional views illustrating a state in which the sensor portion and the injection portion are brought into contact with a user according to one embodiment of the present disclosure. FIGS. 8A and 8B are conceptual diagrams illustrating a state in which a power transmission shaft rotates according to one embodiment of the present disclosure. FIGS. 9A and 9B are conceptual diagrams illustrating a state in which a second needle moves in the injection portion according to one embodiment of the present disclosure.

Referring to FIGS. 1 to 9B, a liquid medicine injection device 1 according to one embodiment of the present disclosure may include a patch portion 100, a sensor portion 200, a stamping portion 300, a first needle holder portion 400, and a sensor mounting portion 500.

Referring to FIGS. 2, 6A to 6C, and 7A to 7C, the patch portion 100 according to one embodiment of the present disclosure is a portion configured to inject a drug into the body through a skin S of a user, and may include an injection portion 110 and an attachment portion 120.

In the patch portion 100 according to one embodiment of the present disclosure, a sensor mounting groove 102 may be formed in the shape of a groove so that the sensor portion 200 to be mounted on the sensor mounting portion 500, which will be described below, is attachable to and detachable from the sensor mounting portion 500. Due to the sensor portion 200, blood glucose of the user may be periodically measured.

In the patch portion 100 according to one embodiment of the present disclosure, a separate driving portion (not designated by a reference numeral) may be installed and an accommodation portion (not designated by a reference numeral) in which a predetermined liquid medicine is accommodated may be installed.

The driving portion installed in the patch portion 100 according to one embodiment of the present disclosure may periodically inject the liquid medicine into the body of the user by a predetermined amount at a predetermined time interval in a pumping manner.

Specifically, the injection portion 110 according to one embodiment of the present disclosure may receive the liquid medicine from the accommodation portion by the driving of the driving portion, and inject the liquid medicine into the body of the user by a predetermined amount at a predetermined time interval.

The patch portion 100 according to one embodiment of the present disclosure is attachable to and detachable from the stamping portion 300, specifically, a patch holder portion 350, which will be described below, and the user may press the stamping portion 300 in the state in which the patch portion 100 is mounted on the stamping portion 300 to bring the patch portion 100 into contact with the skin S of the user.

When the user separates the stamping portion 300 from the skin S while holding the stamping portion 300, the patch portion 100, specifically, the attachment portion 120 to be described below, is brought into contact with the skin S of the user, and due to an adhesive material (not shown in the drawing) attached to the attachment portion 120, a state in which the patch portion 100 is adhered to the skin S of the user may be maintained.

Referring to FIGS. 5 and 7A to 7C, the injection portion 110 according to one embodiment of the present disclosure is disposed inside the patch portion 100, and may receive the liquid medicine accommodated in the accommodation portion by a predetermined amount at a predetermined time interval by the driving of the driving portion and inject the liquid medicine into the body of the user.

Referring to FIG. 5, the injection portion 110 according to one embodiment of the present disclosure may include an injection cover 111, an injection housing 113, a tube portion 115, a second needle holder portion 116, an elastic member 119*e*, and a sealing member 119*s*.

Referring to FIG. 2, the injection cover 111 according to one embodiment of the present disclosure is connected to a power transmission portion 370 to be described below, and specifically, may receive power from a power transmission shaft 371 and rotate in a clockwise direction or a counterclockwise direction.

Referring to FIGS. 2 and 5, an insertion groove 112 may be formed in the injection cover 111 according to one embodiment of the present disclosure.

Specifically, the insertion groove 112 may be formed in one surface (an upper surface based on FIG. 5) of the injection cover 111, which faces the power transmission shaft 371, in the shape of a groove to correspond to the shape of a protrusion 379 protruding from a lower end portion (based on FIG. 2) of the power transmission shaft 371.

In the present disclosure, the insertion groove 112 may be formed in the shape of a groove in the injection cover 111, and the protrusion 379 may be formed to protrude from one surface of the power transmission portion 370, which faces the insertion groove 112, to correspond to the insertion groove 112.

However, but the present disclosure is not limited thereto, and various modifications are possible, such as, a protrusion is formed to protrude from the injection cover 111, and an insertion groove is formed on one surface of the power transmission portion 370 (a lower surface based on FIG. 2) facing the protrusion.

The insertion groove 112 according to one embodiment of the present disclosure may be formed as one or more insertion grooves 112, and specifically, may be formed to correspond to the number of protrusions 379 formed on the power transmission shaft 371.

Referring to FIG. 5, the injection housing 113 according to one embodiment of the present disclosure is coupled to the injection cover 111, and may have an interior formed in a hollow. The second needle holder portion 116, which will be described below, may move in the injection housing 113 in a predetermined direction (a vertical direction based on FIG. 5).

In the present disclosure, the injection housing 113 is formed in a cylindrical shape, but the present disclosure is not limited thereto, and various modifications are possible within the technical spirit in which the second needle holder portion 116 may move in the vertical direction (based on FIG. 5).

Referring to FIG. 5, the injection housing 113 according to one embodiment of the present disclosure may be coupled to the injection cover 111, and may rotate in the clockwise or counterclockwise direction about a longitudinal central axis by being interworked with the rotation of the injection cover 111.

Referring to FIGS. 5, 9A, and 9B, a stepped portion 114 may be formed on an inner circumferential surface of the injection housing 113 according to one embodiment of the present disclosure.

Specifically, the stepped portion 114 may be formed on the inner circumferential surface of the injection housing 113, which faces a stopper 117 formed to protrude from the second needle holder portion 116 to be described below, such that the stopper 117 is held on the stepped portion 114.

The stepped portion 114 may be formed to protrude from the inner circumferential surface of the injection housing 113 toward a center of the injection housing 113. However, the present disclosure is not limited thereto, and the stopper 117 may be formed in the shape of a groove in a direction away from the center of the injection housing 113 within the technical spirit in which the movement of the second needle holder portion 116 is restricted due to the holding of the stopper 117.

Referring to FIGS. 5, 9A, and 9B, the stepped portion 114 according to one embodiment of the present disclosure may be formed in a predetermined section along a circumference of the inner circumferential surface of the injection housing 113 with respect to a longitudinal center of the injection housing 113.

Accordingly, when the injection cover 111 and the injection housing 113 that is coupled to the injection cover 111 rotate in the clockwise direction or the counterclockwise direction about the longitudinal central axis as a rotation central axis, the stepped portion 114 formed on the inner circumferential surface of the injection housing 113 is also rotated, and as the stepped portion 114 rotates, the stopper 117 formed on the second needle holder portion 116 may be spaced apart from the stepped portion 114 to move in an upward direction (based on FIG. 9B).

In other words, as the second needle holder portion 116 moves in the upward direction (based on FIG. 9B) in the injection housing 113, a second needle 118 may be separated from a surface of the skin S of the user, and the tube portion 115 disposed outside the second needle 118 may be maintained in a state of being stuck in the skin S of the user.

In addition, the liquid medicine received from the accommodation portion may be injected into the body through the second needle 118 and the tube portion 115 that is communicating with the second needle 118 by passing through the skin S of the user.

Referring to FIGS. 5, 9A, and 9B, the tube portion 115 according to one embodiment of the present disclosure is installed in the injection housing 113, and may have an interior formed in a hollow. The tube portion 115 may be coupled to and positionally fixed to a tube holder **115*h*, which is coupled to the injection housing 113**.

The second needle 118 may be disposed inside the tube portion 115 according to one embodiment of the present disclosure. Accordingly, when the second needle 118 penetrates the skin S of the user and enters the body, the tube portion 115 may also enter the body of the user together therewith, and when the second needle holder portion 116 and the second needle 118 installed in the second needle holder portion 116 are separated from the user, the tube portion 115 may be positionally fixed while being stuck in the skin S of the user.

Referring to FIG. 5, the tube portion 115 according to one embodiment of the present disclosure passes through the tube holder **115*h* and is coupled to the injection housing 113. In the present disclosure, the tube holder 115*h* and the tube portion 115 are independently provided as separate components, but the present disclosure is not limited thereto, and various modifications are possible such as the tube holder 115*h* and the tube portion 115 are integrally formed and installed in the injection housing 113**.

Referring to FIGS. 2, 9A, and 9B, the second needle holder portion 116 according to one embodiment of the present disclosure is a portion in which the second needle 118 insertable into the tube portion 115 installed, and may be disposed to be movable inside the injection housing 113.

The second needle holder portion 116 according to one embodiment of the present disclosure shares a rotation central axis with the injection cover 111 and the injection housing 113, and may be relatively rotated with respect to the injection cover 111 and the injection housing 113.

The stopper 117 may be formed to protrude from an outer circumferential surface of the second needle holder portion 116 in a direction toward the inner circumferential surface of the injection housing 113, that is, in a direction toward the stepped portion 114 formed on the inner circumferential surface of the injection housing 113. Accordingly, the stopper 117 may be held on the stepped portion 114 formed on the inner circumferential surface of the injection housing 113.

Referring to FIGS. 5, 9A, and 9B, the stopper 117 formed on the second needle holder portion 116 according to one embodiment of the present disclosure and the stepped portion 114 formed on the inner circumferential surface of the injection housing 113 may be released from the holding, and the elastic member **119*e*, which will be described below, may move the second needle holder portion 116 in a direction (in an upward direction based on FIG. 9B) away from a bottom surface (based on FIG. 5) of the injection housing 113**.

Accordingly, the second needle 118 may be separated from the user while the tube portion 115 installed in the injection housing 113 is stuck in the skin S of the user, and the liquid medicine may be injected into the body of the user through the second needle 118, which is connected to the accommodation portion and has a hollow interior, and the tube portion 115 into which the second needle 118 is inserted.

In the present disclosure, when the second needle holder portion 116 is positionally fixed to the inside of the injection housing 113, and the injection housing 113 and the injection cover 111 coupled to the injection housing 113 rotate in the clockwise direction or the counterclockwise direction, the second needle holder portion 116 in which the second needle 118 is installed may move in a predetermined direction while the holding between the second needle holder portion 116 and the injection housing 113 is released.

However, the present disclosure is not limited thereto, and various modifications are possible, such as the injection cover 111 coupled to the injection housing 113 and the injection housing 113 are positionally fixed, and the second needle holder portion 116 rotates inside the injection housing 113, the holding between the second needle holder portion 116 and the injection housing 113 is released, and the like.

Referring to FIGS. 5, 9A, and 9B, according to one embodiment of the present disclosure, the elastic member **119*e* to be described below may be disposed between the second needle holder portion 116 and the injection housing 113, and the second needle holder portion 116 may move in a predetermined direction (upward direction from a lower side based on FIG. 9B) from the injection housing 113 by an elastic restoring force of the elastic member 119*e***.

Referring to FIG. 5, the second needle 118 according to one embodiment of the present disclosure is installed in the second needle holder portion 116, and is insertable into the tube portion 115. The other side of the second needle 118, which is opposite to one side of the second needle 118 inserted into the tube portion 115, is connected to the accommodation portion (not shown in the drawing) installed inside the patch portion 100, and may receive the liquid medicine from the accommodation portion.

The second needle 118 has an interior formed in a hollow, and the liquid medicine received from the accommodation portion may flow into the tube portion 115 through an opening formed at an end portion of the second needle 118 and may be injected into the body of the user through the tube portion 115.

Referring to FIGS. 5, 9A, and 9B, the elastic member 119*e* according to one embodiment of the present disclosure is disposed between the second needle holder portion 116 and the injection housing 113, and may elastically support the second needle holder portion 116.

Referring to FIG. 5, the elastic member 119*e* may have an elastic restoring force in a predetermined direction.

Specifically, in the present disclosure, the elastic member 119*e* is disposed between the second needle holder portion 116 and the bottom surface (based on FIG. 5) of the injection housing 113, and may have an elastic restoring force in the upward direction (based on FIG. 5) from the bottom surface of the injection housing 113.

Accordingly, referring to FIGS. 9A and 9B, as the stopper 117 formed on the second needle holder portion 116 is released from the holding of the stepped portion 114 formed on the inner circumferential surface of the injection housing 113, the second needle holder portion 116 may move in the upward direction (based on FIG. 9B) in the injection housing 113 by the restoring force of the elastic member 119*e*.

However, the present disclosure is not limited thereto, and various modifications are possible, such as the elastic member 119*e* may be disposed between the second needle holder portion 116 and the injection cover 111 and may have an elastic restoring force in the upward direction (based on FIG. 9B).

Referring to FIG. 5, the elastic member 119*e* is formed as a coil spring, but the present disclosure is not limited thereto, and various modifications are possible such as a plate spring within the technical spirit in which the second needle holder portion 116 is elastically supported in a predetermined direction.

Referring to FIGS. 5, 9A, and 9B, the sealing member 119*s* according to one embodiment of the present disclosure is coupled along an outer circumferential surface of the injection cover 111, and may be disposed to surround a region in which the injection cover 111 and a patch housing 101 of the patch portion 100 are connected.

Accordingly, the injection portion 110, which is a coupling structure of the injection cover 111 and the injection housing 113, may come into close contact with the patch housing 101 and rotate stably about the longitudinal central axis of the injection portion 110 as a rotation central axis.

The sealing member 119*s* according to one embodiment of the present disclosure may be formed of a rubber material, and the sealing member 119*s* may come into close contact with both the injection cover 111 and the patch housing 101, thereby improving airtightness between the injection portion 110 and the patch housing 101.

Referring to FIG. 2, the attachment portion 120 according to one embodiment of the present disclosure is disposed outside the patch portion 100, and specifically, may be disposed outside the patch housing 101. The attachment portion 120 may be disposed on each of front, rear, left, and right surfaces of the patch portion 100, and may be foldably coupled to the patch housing 101.

Accordingly, when the user places the stamping portion 300 on the skin S of the user and pushes the stamping portion 300, the patch portion 100 disposed inside of the stamping portion 300 is brought into contact with the skin S of the user, and when the user moves the stamping portion 300 in a direction away from the skin S, the attachment portion 120 is unfolded in a direction away from patch housing 101.

An adhesive material (not shown in the drawing) may be applied to the attachment portion 120. Accordingly, when the attachment portion 120 is unfolded from the patch housing 101 and brought into contact with the skin S of the user, the attachment portion 120 may be adhered to the skin S of the user, and the patch portion 100 may be positionally fixed on the skin S of the user.

Referring to FIGS. 1,2, 4, 6A to 6C, and 7A to 7C, the sensor portion 200 according to one embodiment of the present disclosure is mountable on the patch portion 100, and may include a sensor module 210 and a sensor cover 230.

Referring to FIGS. 6A and 7A, the sensor module 210 according to one embodiment of the present disclosure may include a sensor needle 211 that is disposed inside a first needle 301 to be described below.

The sensor module 210 according to one embodiment of the present disclosure may be formed as a continuous glucose monitoring (CGM) sensor, and the sensor needle 211 may continuously measure blood glucose of the user as the sensor needle 211 passes through the skin S of the user and is stuck in the skin S.

The general configuration of the sensor module 210, which includes the sensor needle 211 and formed of a CGM sensor, is known, and thus, a detailed description related to the sensor module 210 will be omitted.

Referring to FIGS. 1, 2, and 4, the sensor cover 230 according to one embodiment of the present disclosure is coupled to the sensor module 210, and may cover the sensor module 210. The sensor cover 230 is attachable to and detachable from the patch portion 100, specifically the sensor mounting groove 102, and accordingly, the sensor module 210 is mounted on and positionally fixed to the patch portion 100.

In addition, the sensor cover 230 prevents the sensor module 210 from being damaged by an external impact.

Referring to FIGS. 1, 2, and 4, the sensor cover 230 to which the sensor module 210 according to one embodiment of the present disclosure is coupled may be detachably coupled to the sensor mounting portion 500 to be described below, specifically, a groove (not designated by a reference numeral) formed in an inner case 530.

Referring to FIGS. 6A and 6B, when the stamping portion 300 is connected to the sensor mounting portion 500, and the user pushes the stamping portion 300 toward the sensor mounting portion 500, the coupling between the sensor mounting portion 500, specifically the inner case 530, and the sensor cover 230 may be released, and a coupling between the sensor cover 230 and the sensor mounting groove 102 that is formed in the patch portion 100 may be formed.

Accordingly, the sensor portion 200 may be spaced apart from the sensor mounting portion 500, specifically the inner case 530, and stably coupled to the patch portion 100.

Referring to FIGS. 1, 2, 3, 6A, 7A, 8A, and 9A, the stamping portion 300 according to one embodiment of the present disclosure is a portion to which the patch portion 100 is mounted, and may include the first needle 301 connectable to the sensor portion 200.

Referring to FIGS. 2 and 3, the stamping portion 300 according to one embodiment of the present disclosure may include a first body 310, a second body 330, the patch holder portion 350, the power transmission portion 370, and a shaft cover 390.

Referring to FIGS. 2 and 3, the first body 310 according to one embodiment of the present disclosure forms an exterior of the stamping portion 300, and the user may grasp first body 310.

The second body 330 according to one embodiment of the present disclosure is relatively movable inside the first body 310, and when the user pushes the stamping portion 300, the first body 310 is movable in a downward direction (based on FIG. 6B) on the second body 330 that is in a state of being in contact with the skin S of the user.

Referring to FIGS. 2 and 3, the patch holder portion 350 according to one embodiment of the present disclosure is connected to the second body 330, and may be disposed to be spaced apart from the first body 310 by a predetermined separation distance, and the patch portion 100 may be seated in the second body 330.

Referring to FIGS. 2, 3, 6A, and 7A, on the patch holder portion 350 according to one embodiment of the present disclosure, a movement control portion 351, which is disposed between a shaft holder portion 373 to be described below, specifically, a shaft holder body 374 and an inner wall of the second body 330 and between the first needle holder portion 400 and the inner wall of the second body 330 and configured to control the movement of the shaft holder portion 373 and the first needle holder portion 400, may be formed to protrude.

Referring to FIG. 2, the movement control portion 351 according to one embodiment of the present disclosure may be provided in a plural number, and referring to FIG. 2, four movement control portions 351 may be formed in front, rear, left, and right sides of each of the shaft holder body 374 and a first needle holder body 410 to be described below to control the movement of each of the shaft holder body 374 and the first needle holder body 410.

Referring to FIGS. 7A to 7C, in the movement control portion 351 according to one embodiment of the present disclosure, one surface facing each of the shaft holder body 374 and the first needle holder body 410 may be formed to be inclined.

One surface of each of the shaft holder body 374 and the first needle holder body 410, which faces the one surface of the movement control portion 351 formed to be inclined, may also be formed to be inclined to correspond to the one surface of the movement control portion 351 so as to be in surface contact with the one surface of the movement control portion 351 formed to be inclined.

Accordingly, the shaft holder body 374 and the first needle holder body 410 may each move stably along the inclined surface when the shaft holder body 374 and the first needle holder body 410 move in a direction away from the patch holder portion 350 due to elastic restoring forces of elastic members 376 and 430 to be described below.

Referring to FIGS. 2, 3, 7A, and 7B, the power transmission portion 370 according to one embodiment of the present disclosure may connect between the first body 310 and the patch holder portion 350, and transmit power to the injection portion 110 to separate the second needle 118 connected to the injection portion 110 from the skin S of the user.

The power transmission portion 370 according to one embodiment of the present disclosure may include the power transmission shaft 371, the shaft holder portion 373, and the elastic member 376.

The power transmission shaft 371 according to one embodiment of the present disclosure is rotatable in the clockwise direction or the counterclockwise direction about the longitudinal central axis as a rotation central axis, is connected to the injection portion 110, and may transmit rotational power to the injection portion 110, specifically the injection cover 111 and the injection housing 113.

Referring to FIGS. 2, 3, and 7A to 7C, at least one protrusion 379 protruding toward the injection portion 110 may be formed at one end portion of the power transmission shaft 371, which is directed to the injection portion 110, according to one embodiment of the present disclosure.

The protrusion 379 according to one embodiment of the present disclosure may be formed to protrude to correspond to the shape of the insertion groove 112 formed in the injection portion 110, specifically the injection cover 111, and when the patch portion 100 is mounted to the patch holder portion 350, the protrusion 379 may be inserted into the insertion groove formed in the injection cover 111, and the power transmission shaft 371 may be connected to the patch portion 100, specifically the injection portion 110.

Accordingly, when the power transmission shaft 371 rotates in the clockwise direction or the counterclockwise direction about the longitudinal central axis as a rotation central axis, the injection portion 110 connected to the power transmission shaft 371, specifically the injection housing 113 connected to the injection cover 111 and the injection cover 111 may be rotated in the clockwise direction or the counterclockwise direction.

The protrusion 379 and the insertion groove 112 according to one embodiment of the present disclosure, may each be provided in a plural number, and the plurality of protrusions 379 and the plurality of insertion grooves 112 may be equiangularly disposed with respect to a longitudinal central axis of the power transmission shaft 371 and the injection cover 111.

Referring to FIGS. 2, 3, 7A to 7C, 8A, and 8B, the power transmission shaft 371 according to one embodiment of the present disclosure may be formed to extend in a longitudinal direction and may rotate about the longitudinal central axis in the clockwise direction or the counterclockwise direction.

The power transmission shaft 371 is disposed between the first body 310 and the patch holder portion 350, and allows the first body 310 and the patch holder portion 350 to be spaced apart from each other by as much as a length of the power transmission shaft 371.

Accordingly, the second body 330 is relatively movable with respect to the first body 310 in up and down directions on the first body 310 and the patch holder portion 350.

Referring to FIGS. 2, 3, 7A to 7C, 8A, and 8B, the shaft holder portion 373 according to one embodiment of the present disclosure is connected to the power transmission shaft 371, and is movable on the power transmission shaft 371.

Referring to FIGS. 2, 3, 7A, and FIG. 8A, a rotation guide groove 372 may be formed in the power transmission shaft 371 according to one embodiment of the present disclosure, and a guide body 375 may be formed to protrude from the shaft holder portion 373, specifically the shaft holder body 374, toward the rotation guide groove 372.

Referring to FIGS. 8A and 8B, the guide body 375 formed to protrude from the shaft holder body 374 toward the power transmission shaft 371 may be seated in the rotation guide groove 372. The guide body 375 formed on the shaft holder body 374 is movable only on a predetermined linear path.

Referring to FIGS. 7A to 7C, the elastic member 376 according to one embodiment of the present disclosure may be disposed between the shaft holder body 374 and the patch holder portion 350, and may elastically support the shaft holder body 374 in a direction (upward direction based on FIG. 7A) away from the patch holder portion 350.

Referring to FIGS. 7A to 7C, the elastic member 376 according to one embodiment of the present disclosure may move the shaft holder body 374 by pushing the shaft holder body 374 in the direction away from the patch holder portion 350 (upward direction based on FIG. 7C) when the patch holder portion 350 disposed between the shaft holder body 374 and the second body 330, specifically, the movement control portion 351 is spaced apart from the second body 330 as the second body 330 relatively moves with respect to the first body 310.

Referring to FIGS. 8A and 8B, as the shaft holder body 374 moves in the upward direction, the guide body 375 formed to protrude from an inner circumferential surface of the shaft holder body 374 may move in upward and downward directions (based on FIG. 8B) only on the predetermined linear path and rotate the power transmission shaft 371 in the clockwise direction or the counterclockwise direction.

Referring to FIGS. 2, 3, 8A, and 8B, the rotation guide groove 372 according to one embodiment of the present disclosure may be formed at a predetermined angle with respect to the longitudinal direction of the power transmission shaft 371 in a predetermined section along the longitudinal direction of the power transmission shaft 371.

Specifically, two or more linear paths formed in parallel to each other may be formed in the rotation guide groove 372, and a portion connecting the two or more linear paths may be formed to be bent.

Accordingly, while the guide body 375 moves along the rotation guide groove 372, the guide body 375 moves on the different linear path of the rotation guide groove 372, and since the position of the guide body 375 is fixed, the power transmission shaft 371 in which the rotation guide groove 372 is formed may rotate about the longitudinal central axis in the clockwise direction or the counterclockwise direction.

In addition, as the power transmission shaft 371 rotate in the clockwise direction or the counterclockwise direction, the patch portion 100, the injection portion 110 connected to the power transmission shaft 371, specifically, the injection cover 111, and the injection housing 113 to which the injection cover 111 is coupled may rotate in the clockwise direction or the counterclockwise direction.

Referring to FIGS. 2 and 3, the shaft cover 390 according to one embodiment of the present disclosure is coupled to the first body 310, and may be coupled to the power transmission shaft 371.

Referring to FIGS. 2, 3, 6A, 6B, and 7A to 7C, the first needle holder portion 400 according to one embodiment of the present disclosure is a portion to which the first needle 301 is installed, and is relatively movable with respect to the patch holder portion 350.

The first needle holder portion 400 according to one embodiment of the present disclosure may include the first needle holder body 410 and the elastic member 430.

The first needle 301 may be positionally fixed to the first needle holder body 410, the elastic member 430 may be in contact with and support the first needle holder body 410 and the patch holder portion 350 and elastically support the first needle holder body 410 in a direction away from the patch holder portion 350.

The first needle holder body 410 may be in surface contact with the movement control portion 351 formed on the patch holder portion 350, and an outer circumferential surface of the first needle holder body 410, which is in surface contact with the movement control portion 351, may be formed to be inclined.

One surface of the movement control portion 351, which is in surface contact with the outer circumferential surface of the first needle holder body 410 formed to be inclined, may also be formed to be inclined.

Accordingly, the first needle holder body 410 may move stably along the surface formed to be inclined when the first needle holder body 410 moves in a direction away from the patch holder portion 350 by the elastic restoring force of the elastic member 430.

The first needle 301 formed in the first needle holder body 410 may have an interior formed in a hollow, and the sensor module 210, specifically the sensor needle 211, may be disposed inside the first needle 301.

Accordingly, the first needle 301 having the sensor needle 211 disposed therein passes through the skin S of the user and is stuck in the skin S, and as the user pushes the stamping portion 300, specifically, the first body 310, the first needle holder body 410 moves upward (based on FIG. 7B) by the elastic restoring force of the elastic member 430, and accordingly, the first needle 301 moves together with the first needle holder body 410. Thus, blood glucose may be continuously measured in the state in which the sensor needle 211 is still stuck in the skin S of the user.

Referring to FIGS. 1, 2, 4, 6A, and 6B, the sensor mounting portion 500 according to one embodiment of the present disclosure is couplable to the stamping portion 300, and the sensor portion 200 may be formed to protrude from one surface of the sensor mounting portion 500, which faces the patch portion 100 on which the sensor mounting groove 102 is formed.

In the present disclosure, the sensor portion 200 is disposed to protrude from one surface of the sensor mounting portion 500 facing the patch portion 100, but the present disclosure is not limited thereto, and various modifications are possible within the technical spirit in which the sensor portion 200 disposed on the sensor mounting portion 500 is mounted in the sensor mounting groove 102 formed in the patch portion 100 when the stamping portion 300 is coupled to the sensor mounting portion 500.

Referring to FIGS. 1, 2, 4, 6A, and 6B, the sensor mounting portion 500 according to one embodiment of the present disclosure may include an outer case 510 and the inner case 530. The outer case 510 has one side (upper side based on FIG. 1) that is open, and may be formed to be contactable the stamping portion 300.

The inner case 530 according to one embodiment of the present disclosure is disposed inside the outer case 510, and the sensor portion 200 may be seated in the inner case 530.

Referring to FIGS. 1, 2, and 4, on an inner circumferential surface of the outer case 510 according to one embodiment of the present disclosure, a holding protrusion 513 may be formed to protrude in an outward direction, specifically, in a protruding direction from the inner circumferential surface of the outer case 510.

On an outer circumferential surface of the inner case 530 according to one embodiment of the present disclosure, a holding portion 533 may be formed to protrude so as to be held on the holding protrusion 513, which is formed on the inner circumferential surface of the outer case 510, as the inner case 530 is inserted into the outer case 510. Accordingly, it is possible to prevent the inner case 530 from being separated from the outer case 510.

Referring to FIGS. 1, 2, and 4, a rib portion 511 protruding in a direction toward the inner case 530 may be formed on the outer case 510 according to one embodiment of the present disclosure to extend in a longitudinal direction (vertical direction based on FIG. 1), and a rib guide 531 in which a groove is formed along the longitudinal direction (vertical direction based on FIG. 1) may be formed on an inner surface of the inner case 530 facing the rib portion 511 such that the rib portion 511 is seated in the rib guide 531.

Accordingly, the rib portion 511 formed on the outer case 510 is inserted into the rib guide 531 formed on the inner case 530, specifically, the groove formed along the longitudinal direction, and the inner case 530 may stably move along the longitudinal direction (vertical direction based on FIG. 1) with respect to the outer case 510.

The operation principle and effect of the above-described liquid medicine injection device 1 according to one embodiment of the present disclosure will be described.

Referring to FIGS. 1 to 9B, the liquid medicine injection device 1 according to one embodiment of the present disclosure may include the patch portion 100, the sensor portion 200, the stamping portion 300, the first needle holder portion 400, and the sensor mounting portion 500.

Referring to FIGS. 1, 2, and 4, the sensor mounting portion 500 may include the outer case 510 and the inner case 530, and the sensor portion 200 may be mounted on one surface (upper surface based on FIG. 1) of the inner case 530.

The sensor portion 200 according to one embodiment of the present disclosure does not maintain the state of being attached on the patch portion 100, but is stored in a state of being mounted on the sensor mounting portion 500, and when the user intends to attach the patch portion 100 to the skin S, the sensor portion 200 may be moved from the sensor mounting portion 500 to the patch portion 100 mounted on the stamping portion 300.

Accordingly, a sterilization state of the sensor portion 200 for continuously measuring blood glucose may be maintained.

Referring to FIGS. 6A and 6B, the stamping portion 300 may be coupled to the sensor mounting portion 500 in the state in which the sensor portion 200 according to one embodiment of the present disclosure is mounted to the sensor mounting portion 500.

The user grips the stamping portion 300, specifically the first body 310 to allow the second body 330 disposed inside the first body 310 to be disposed inside the sensor mounting portion 500, specifically the inner case 530.

Referring to FIGS. 6A and 6B, the user may dispose the stamping portion 300 on the sensor mounting portion 500 such that one surface of the stamping portion 300, which is formed along a circumference of an outer circumferential surface of the first body 310, and one surface of the sensor mounting portion 500, which is formed along a circumference of an outer circumferential surface of the outer case 510, are brought into surface contact with each other.

Referring to FIGS. 6A and 6B, the user may push the first body 310 in the downward direction (based on FIG. 6B) in the state in which the stamping portion 300 is disposed on the sensor mounting portion 500.

Referring to FIG. 6B, when the user pushes the stamping portion 300, the first body 310 and the patch holder portion 350, which is connected to the first body 310 through the power transmission shaft 371, move in the downward direction (based on FIG. 6B) on the second body 330.

In addition, referring to FIG. 6B, a lower end portion of the second body 330 is inserted into the groove formed in the inner case 530, and here, when the user pushes the first body 310 again, the inner case 530 moves in the downward direction (based on FIG. 6B) inside the outer case 510.

Referring to FIG. 6B, the stamping portion 300, specifically, one surface formed along the circumference of the outer circumferential surface of the first body 310, and one surface formed along the circumference of the outer circumferential surface of the outer case 510 are brought into surface contact with each other. The sensor portion 200 mounted on one surface of the inner case 530 may be mounted in the sensor mounting groove 102 formed in the patch portion 100.

Referring to FIG. 6C, after the sensor portion 200 mounted on the sensor mounting portion 500 according to one embodiment of the present disclosure is mounted in the sensor mounting groove 102 formed in the patch portion 100, the user may grip the stamping portion 300 to separate the stamping portion 300 from the sensor mounting portion 500.

Referring to FIGS. 6C and 7A, the sensor portion 200 may be mounted on the patch portion 100 that is mounted on the stamping portion 300, specifically the patch holder portion 350, and the first needle 301 installed in the stamping portion 300 and having a hollow interior may be disposed outside the sensor needle 211.

Referring to FIG. 7A, the sensor portion 200 is in a state of being mounted on the patch portion 100 according to one embodiment of the present disclosure, and the sensor needle 211 may be disposed inside the first needle 301 that is installed in the stamping portion 300.

Referring to FIGS. 5 and 7*a*, the injection portion 110 according to one embodiment of the present disclosure may include the injection cover 111, the injection housing 113, the tube portion 115, the second needle holder portion 116, the elastic member 119*e*, and the sealing member 119*s*.

Referring to FIGS. 7A and 9A, the stopper 117 formed on the second needle holder portion 116 on which the second needle 118 is installed is held on the stepped portion 114 that is formed in a predetermined section along the circumference of the inner circumferential surface of the injection housing 113.

Referring to FIG. 9A, since the stopper 117 is held on the stepped portion 114, the second needle holder portion 116 is limited in movement in the upward direction (based on FIG. 9A), and the second needle 118 may be disposed inside the tube portion 115 that is coupled to the injection housing 113.

Referring to FIGS. 7A and 9A, although the elastic member 119*e* is disposed in a compressed state between the second needle holder portion 116 and the bottom surface (based on FIG. 9A) of the injection housing 113, and the elastic member 119*e* has an elastic restoring force in a direction (upward direction from the lower side based on FIG. 9A) in which the second needle holder portion 116 is spaced apart from the bottom surface of the injection housing 113, since the stopper 117 is held on the stepped portion 114, the compressed state may be maintained.

Referring to FIGS. 7A and 7B, the user may bring the second body 330 into contact with the skin S of the user while gripping the stamping portion 300, specifically the first body 310. Thereafter, the user may push the first body 310 in a direction toward the skin S of the user (downward direction based on FIG. 7B).

Referring to FIG. 7B, as the user pushes the first body 310, the first body 310 and the patch holder portion 350, which is coupled to the first body 310 while maintaining a constant separation distance, move downward (based on FIG. 7B) along the second body 330 in the state in which the second body 330 is in contact with the skin S of the user.

The first body 310 and the patch holder portion 350 according to one embodiment of the present disclosure are connected to the power transmission portion 370, specifically the power transmission shaft 371, and accordingly, as the first body 310 moves on the second body 330, the patch holder portion 350 on which the patch portion 100 is mounted moves toward the skin S of the user.

Referring to FIGS. 7A and 7B, the first needle 301 disposed outside the sensor needle 211 may be coupled to the first needle holder portion 400, specifically the first needle holder body 410, and the elastic member 430 may be disposed in a compressed state between the first needle holder body 410 and the patch holder portion 350.

At least one movement control portion 351 formed to protrude from the patch holder portion 350 may be disposed between the first needle holder body 410 and the inner wall of the second body 330.

Referring to FIG. 7B, as the first body 310 and the patch holder portion 350 move downward, the movement control portion 351 and the inner wall of the second body 330 are spaced apart from each other, and as the movement control portion 351 is spaced apart from the inner wall of the second body 330, the movement control portion 351 is bent in an outward direction from a center of the first needle holder body 410 by the elastic restoring force of the elastic member 430

Referring to FIG. 7C, the first needle holder body 410 to which the first needle 301 is coupled by the elastic restoring force of the elastic member 430 is spaced apart from the patch holder portion 350 and moves in the upward direction (based on FIG. 7C) in the state in which the first needle 301 and the sensor needle 211 are stuck in the skin S of the user, the state in which the sensor needle 211 is stuck in the skin S of the user is maintained, and the first needle 301 is separated from the skin S of the user.

Referring to FIGS. 7A and 7B, the second needle 118 coupled to the second needle holder portion 116 may be disposed inside the tube portion 115 coupled to the injection housing 113.

Referring to FIG. 9A, the stopper 117 formed to protrude from the second needle holder portion 116 may be held on the stepped portion 114 formed on the inner circumferential surface of the injection housing 113, and the elastic member 119*e* may be disposed in a compressed state between the second needle holder portion 116 and the bottom surface of the injection housing 113.

Referring to FIG. 8A, the guide body 375 formed to protrude from the inner circumferential surface of the shaft holder body 374 may be seated in the rotation guide groove 372 formed in the power transmission shaft 371, and at least one movement control portion 351 formed to protrude from the patch holder portion 350 may be disposed between the shaft holder body 374 and the inner wall of the second body 330.

Referring to FIG. 7B, as the first body 310 and the patch holder portion 350 move downward, the movement control portion 351 and the inner wall of the second body 330 are spaced apart from each other, and as the movement control portion 351 is spaced apart from the inner wall of the second body 330, the movement control portion 351 is bent in the outward direction from a center of the shaft holder body 374 by the elastic restoring force of the elastic member 376

Referring to FIGS. 7C and 8B, in the state in which the second needle 118 and the tube portion 115 are stuck in the skin S of the user, the shaft holder body 374 moves in the upward direction (based on FIG. 8B) by the elastic restoring force of the elastic member 376.

Referring to FIGS. 8A and 8B, a position of the guide body 375, which is formed to protrude from the inner circumferential surface of the shaft holder body 374 disposed outside the power transmission shaft 371, is fixed, and the shaft holder body 374 moves in the upward direction by the restoring force of the elastic member 376.

Referring to FIGS. 8A and 8B, since the rotation guide groove 372 is formed at a predetermined angle with respect to the longitudinal direction of the power transmission shaft 371 in a predetermined section along the longitudinal direction of the power transmission shaft 371, when the shaft holder body 374 moves in the upward direction, the power transmission shaft 371 may be rotated in the clockwise direction (from a rightward direction to a leftward direction based on to FIG. 8B).

Since the rotation guide groove 372 is formed at a predetermined angle with respect to the longitudinal direction of the power transmission shaft 371 in a predetermined section along the longitudinal direction of the power transmission shaft 371, a linear movement of the shaft holder body 374 may be converted into a rotational movement of the power transmission shaft 371.

Referring to FIGS. 7C, 8B, and 9B, as the power transmission shaft 371 rotates, the injection cover 111 connected to the power transmission shaft 371 may be rotated. As the injection cover 111 rotates, the injection housing 113 coupled to the injection cover 111 may be rotated.

As the injection cover 111 and the injection housing 113 relatively rotate with respect to the second needle holder portion 116 that is positionally fixed, the stopper 117 formed to protrude from the second needle holder portion 116 may be spaced apart from the stepped portion 114 formed on the inner circumferential surface of the injection housing 113.

As the stopper 117 is spaced apart from the stepped portion 114, the second needle holder portion 116 may be spaced apart from the bottom surface of the injection housing 113 and may move upward (based on FIG. 9B) by the elastic restoring force of the elastic member 119*e*.

Referring to FIG. 7C, in the state in which the second needle 118 and the tube portion 115 are stuck in the skin S of the user, by the elastic restoring force of the elastic member 119*e*, the second needle holder portion 116, to which the second needle 118 is coupled, is spaced apart from the bottom surface of the injection housing 113 and moved in the upward direction (based on FIG. 7C), and the second needle 118 is spaced apart from the skin S of the user while the state in which the tube portion 115 is stuck in the skin S of the user is maintained.

The second needle 118 still maintains the state in communication with the tube portion 115, receives the liquid medicine from the accommodation portion installed in the patch portion 100, and periodically injects the liquid medicine into the body of the user through the second needle 118 and the tube portion 115 by a predetermined amount.

Referring to FIG. 2, the attachment portion 120 on which an adhesive material is applied may be coupled to the patch housing 101 of the patch portion 100 in a folded state.

The patch portion 100 is in contact with the skin S of the user, and as the user lifts the stamping portion 300 so that the stamping portion 300 is separated from the skin S of the user, the patch portion 100 is spaced apart from the patch holder portion 350, and as the patch portion 100 is released from the coupling with patch holder portion 350, the attachment portion 120 is unfolded and attached to the skin S of the user by the adhesive material.

Accordingly, the state in which the patch portion 100 is stably in contact with the skin S of the user is maintained, and the state in which the sensor needle 211 and the tube portion 115 are stuck in the skin S of the user is maintained.

In the liquid medicine injection device 1 according to one embodiment of the present disclosure, the sensor portion 200 and the injection portion 110 are installed in the patch portion 100, which is a single device, and attached to the skin S of the user so that the convenience of use may be improved.

Due to the simple operation of pushing the stamping portion 300 by the user, the stamping portion 300 transmits power to the patch portion 100 so that the first needle 301 and the second needle 118, which is connected to the injection portion 110, are momentarily inserted together into and separated from the skin S of the user, and thus the convenience of use may be improved.

In addition, since the rotation guide groove 372 formed in the power transmission shaft 371 is formed at a predetermined angle with respect to the longitudinal direction of the power transmission shaft 371 in a predetermined section along the longitudinal direction of the power transmission shaft 371, a linear movement of the shaft holder body 374 may be converted into a rotational movement of the power transmission shaft 371.

In addition, since the protrusion 379 formed on the power transmission shaft 371 is inserted into the insertion groove 112 formed in the injection cover 111, as the power transmission shaft 371 rotates, the injection cover 111 is rotated together with the power transmission shaft 371, so that the second needle holder portion 116 on which the second needle 118 is installed may move within the injection housing 113, and the second needle 118 may be separated from the skin S of the user.

Further, since the outer circumferential surface of the first needle holder body 410 comes into surface contact with the movement control portion 351, which is formed on the patch holder portion 350, to be inclined, the first needle holder body 410 may be stably spaced apart from the patch holder portion 350 by the elastic restoring force of the elastic member 430.

Further, since an outer circumferential surface of the shaft holder body 374 comes into surface contact with the movement control portion 351, which is formed on the patch holder portion 350, to be inclined, the shaft holder body 374 may be stably spaced apart from the patch holder portion 350 by the elastic restoring force of the elastic member 376.

Further, the airtightness between the injection portion 110 and the patch housing 101 may be improved due to the sealing member 119*s*.

Figure 10:
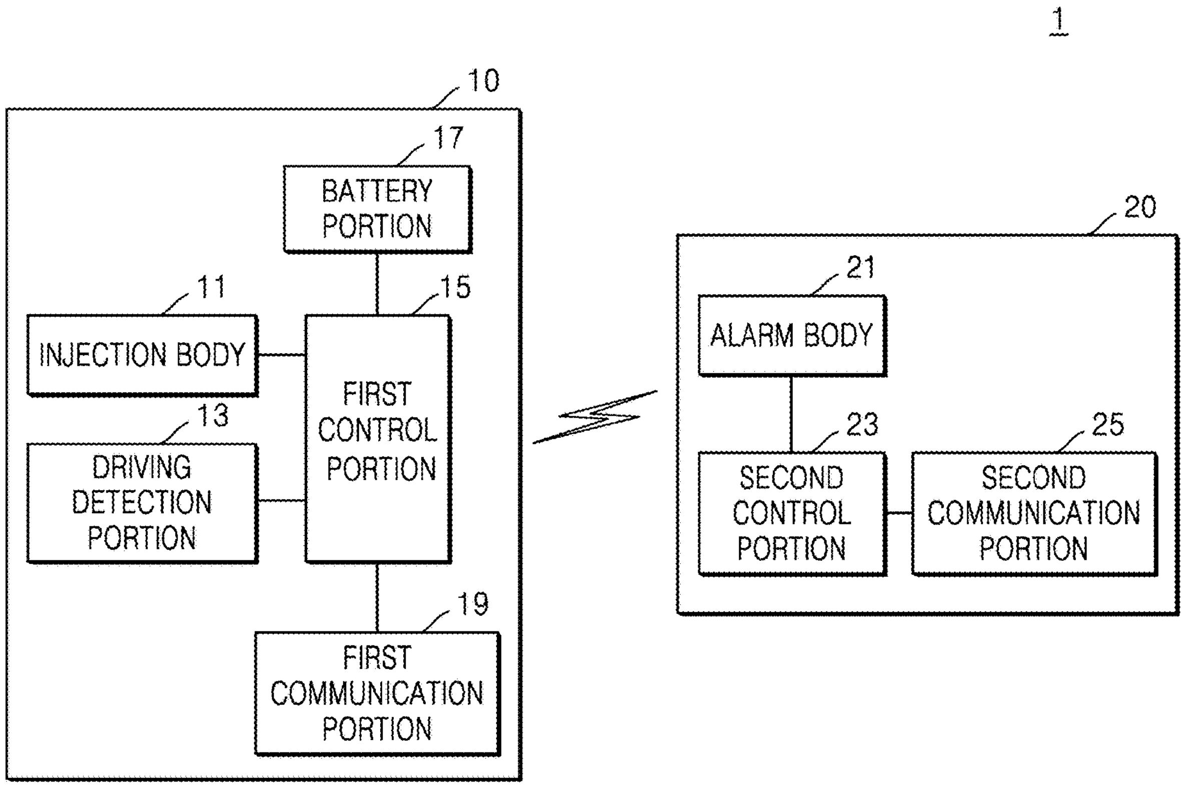
FIG. 10 is a block diagram illustrating a liquid medicine injection device according to one embodiment of the present disclosure.
Figure 11:
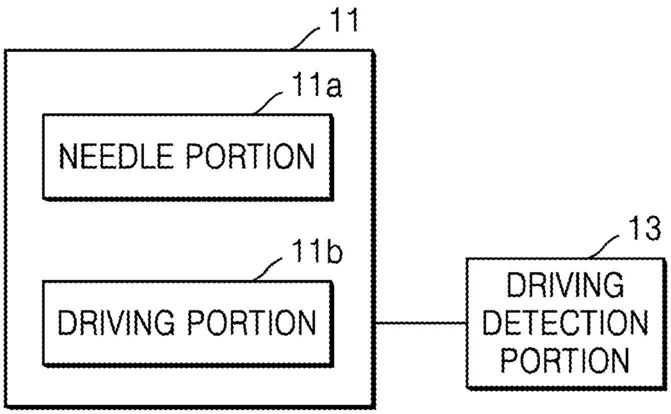
FIG. 11 is a block diagram illustrating an injection body according to one embodiment of the present disclosure.
Figure 12:
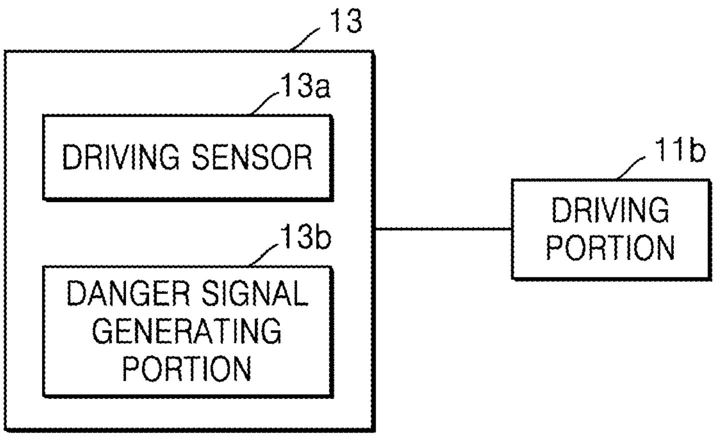
FIG. 12 is a block diagram illustrating a driving detection portion according to one embodiment of the present disclosure.
Figure 13:
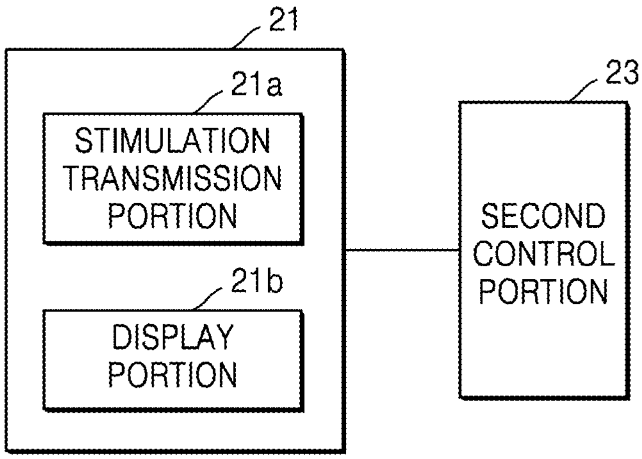
FIG. 13 is a block diagram illustrating an alarm body according to one embodiment of the present disclosure.
Figure 14:
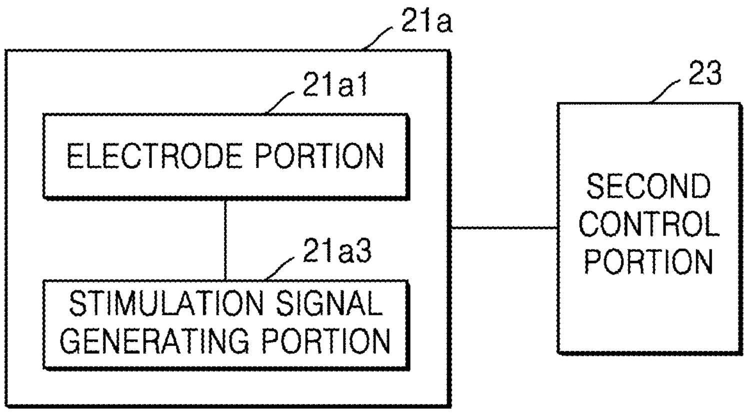
FIG. 14 is a block diagram illustrating a stimulation transmission portion according to one embodiment of the present disclosure.
Figure 15:
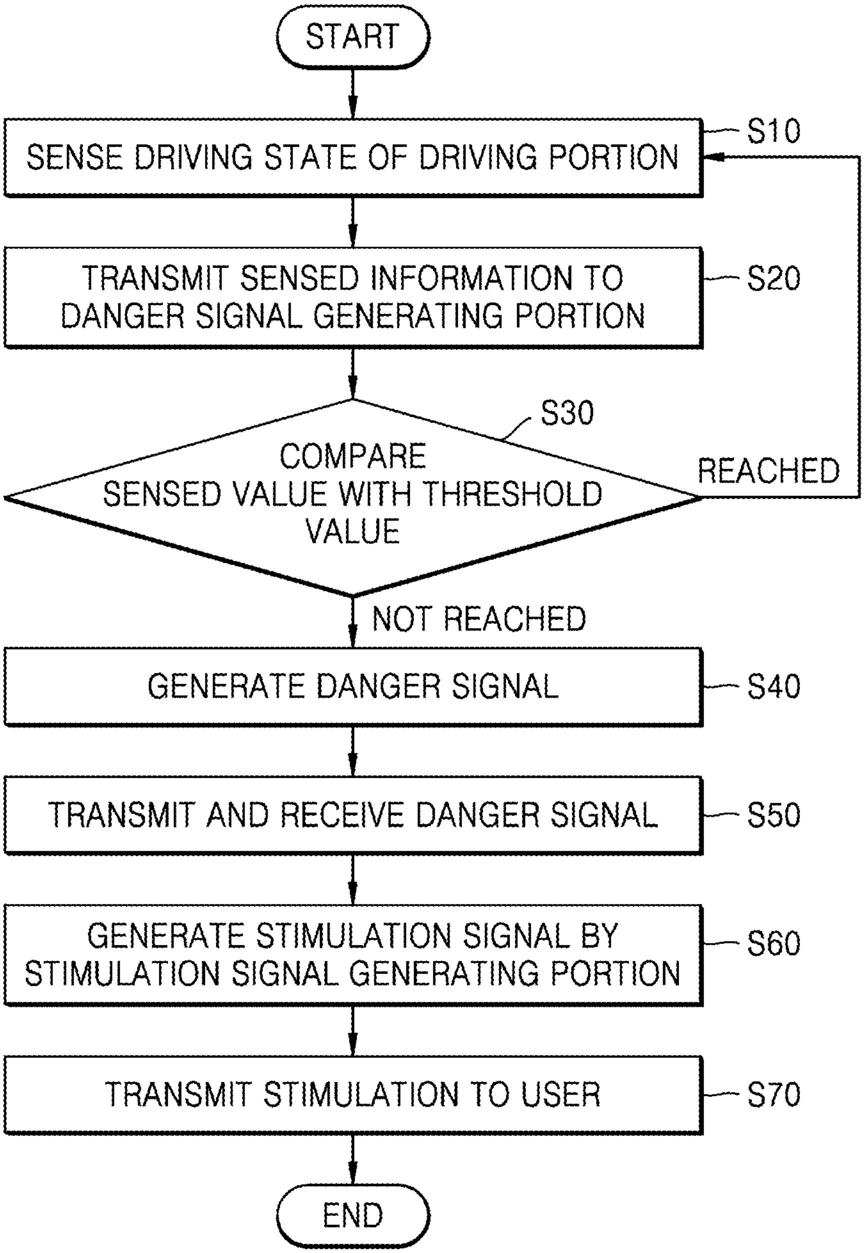
FIG. 15 is a flowchart illustrating an alarming method of the liquid medicine injection device of the present disclosure.
Figure 16:
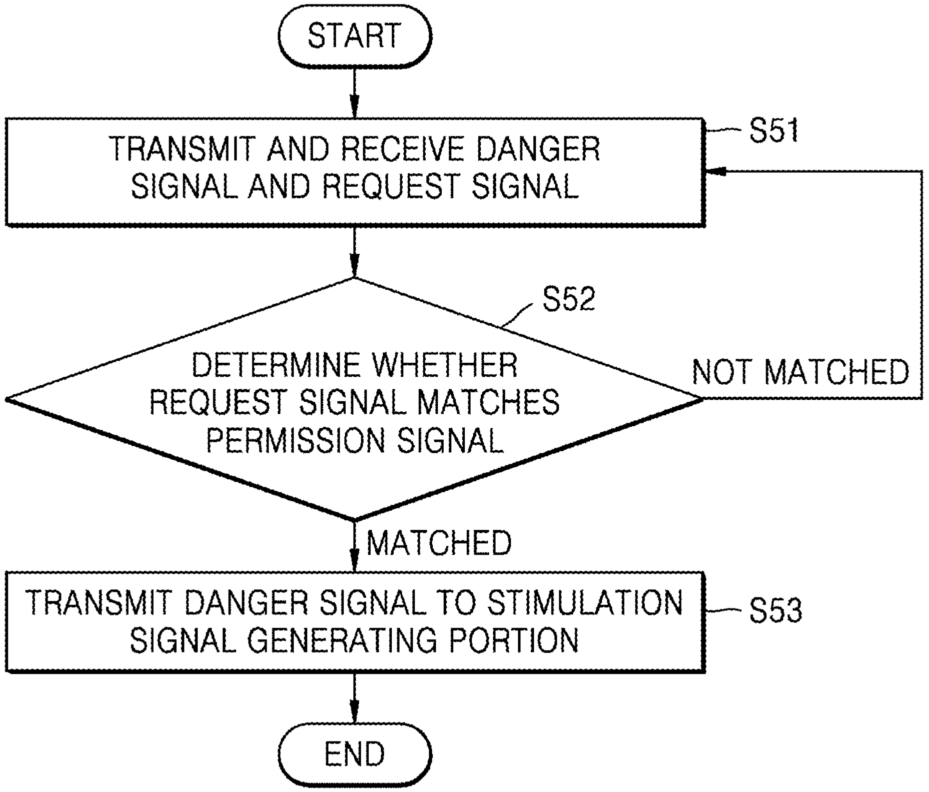
FIG. 16 is a flowchart illustrating the operation of a second control portion according to one embodiment of the present disclosure.
Figure 17:
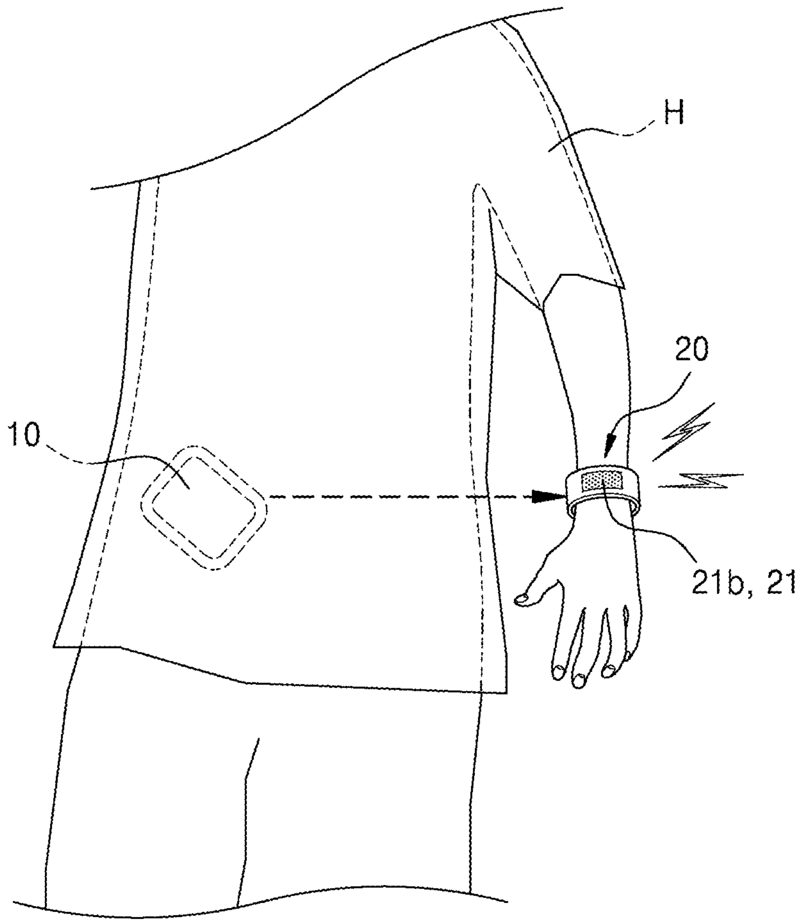
FIG. 17 is a view illustrating a use state of the liquid medicine injection device according to one embodiment of the present disclosure.

FIG. 10 is a block diagram illustrating a liquid medicine injection device according to one embodiment of the present disclosure. FIG. 11 is a block diagram illustrating an injection body according to one embodiment of the present disclosure. FIG. 12 is a block diagram illustrating a driving detection portion according to one embodiment of the present disclosure. FIG. 13 is a block diagram illustrating an alarm body according to one embodiment of the present disclosure. FIG. 14 is a block diagram illustrating a stimulation transmission portion according to one embodiment of the present disclosure. FIG. 15 is a flowchart illustrating an alarming method of the liquid medicine injection device of the present disclosure. FIG. 16 is a flowchart illustrating the operation of a second control portion according to one embodiment of the present disclosure. FIG. 17 is a view illustrating a use state of the liquid medicine injection device according to one embodiment of the present disclosure.

Referring to FIGS. 10 to 17, a liquid medicine injection device 1 according to one embodiment of the present disclosure may include an injection portion 10 and an alarm portion 20.

Referring to FIGS. 10 to 12, the injection portion 10 according to one embodiment of the present disclosure may include an injection body 11, a driving detection portion 13, a first control portion 15, a battery portion 17, and a first communication portion 19.

The injection body 11 according to one embodiment of the present disclosure is a portion configured to inject a liquid medicine into the body of a user H, who is a patient, and specifically, the liquid medicine may be insulin injected into the body of the user H, who is a diabetic patient, particularly a pediatric diabetic patient.

Referring to FIG. 11, the injection body 11 according to one embodiment of the present disclosure may include a needle portion 11*a* and a driving portion 11*b*. The needle portion 11*a* may pass through the skin of the user H to form a flow path through which the liquid medicine accommodated in the injection portion 10 flows into the body of the user.

Although not shown in the drawings, a tube having a hollow interior may be disposed outside the needle portion 11*a*, and when the needle portion 11*a* passes through the skin of the user H, the tube disposed outside the needle portion 11*a* may pass through the skin of the user H together with the needle portion 11*a*, and the liquid medicine may be injected into the body of the user H through the tube formed as a hollow.

Referring to FIG. 11, the driving portion 11*b* according to one embodiment of the present disclosure is electrically connected to the needle portion 11*a*, and may receive a power source from the battery portion 17 and transmit power to the needle portion 11*a* so that the needle portion 11*a* can move.

Although not shown in the drawings, the driving portion 11*b* according to one embodiment of the present disclosure may be formed in the form of a motor or a pump, and the needle portion 11*a* may pass through and permeate the skin of the user H by the driving of the driving portion 11*b*.

Although not shown in the drawings, the driving portion 11*b* according to one embodiment of the present disclosure may include at least one gear, so that the power generated by the driving portion 11*b* is transmitted to the needle portion 11*a* through the gear, and the needle portion 11*a* moves toward into the body of the user H.

In the present disclosure, the driving portion 11*b* moves the needle portion 11*a* in a gear manner, but the present disclosure is not limited thereto. and various modifications are possible within the technical spirit in which the needle portion 11*a* receives power from the driving portion 11*b*, and the needle portion 11*a* passes through the skin of the user H so that the liquid medicine is injected into the body of the user H.

The driving portion 11*b* according to one embodiment of the present disclosure may include a pump, and may supply the liquid medicine, such as insulin, to the tube by the driving of the pump, so that the liquid medicine may be discharged to the outside, that is, into the body of the user H through the flow path formed in the tube.

According to one embodiment of the present disclosure, the driving portion 11*b* may be electrically connected to the driving detection portion 13 to be described below. The driving detection portion 13 may be connected to the injection body 11, specifically the driving portion 11*b*, to detect information on a driving state of the driving portion 11*b*.

By detecting the information on the driving state of the driving portion 11*b* that transmits power to the needle portion 11*a*, it is possible to identify whether the injection body 11, specifically the driving portion 11*b* is operating properly, whether the needle portion 11*a* receiving the power from the driving portion 11*b* moves properly, or the like.

Referring to FIGS. 10 to 12, the driving detection portion 13 according to one embodiment of the present disclosure is electrically connected to the injection body 11, and may detect information on a driving state of the injection body 11.

Referring to FIG. 12, the driving detection portion 13 according to one embodiment of the present disclosure may include a driving sensor 13*a* and a danger signal generating portion 13*b*.

The driving sensor 13*a* according to one embodiment of the present disclosure is electrically connected to the driving portion 11*b*, and may sense the driving state of the driving portion 11*b*.

In the present disclosure, the driving state refers to a state of the driving portion 11*b* for the injection portion 10 to operate normally, and it is possible to sense whether the power is transmitted to the needle portion 11*a* from the driving portion 11*b*, and whether the power source is continuously supplied to the driving portion 11*b*.

The driving sensor 13*a* according to one embodiment of the present disclosure may sense the driving portion 11*b*, specifically the rotation of the gear, and may sense whether the needle portion 11*a*, which receives the power through the gear, normally moves toward the skin of the user H as the gear moves by as much as a predetermined rotation radius.

Further, the driving sensor 13*a* may sense a flow rate of the liquid medicine accommodated in the driving portion 11*b*, specifically the pump, and may sense whether the liquid medicine accommodated in the pump is discharged to the outside by a predetermined amount at a predetermined time interval.

The driving sensor 13*a* according to one embodiment of the present disclosure may sense a voltage of the battery portion 17 that supplies the power source to the liquid medicine injection device. The driving sensor 13*a* may periodically check the voltage of the battery portion 17, and when the voltage of the battery portion 17 is measured to be lower than a predetermined voltage, the driving sensor 13*a* may transmit information related thereto to the danger signal generating portion 13*b* to be described below.

Referring to FIG. 12, the danger signal generating portion 13*b* according to one embodiment of the present disclosure may generate a danger signal on the basis of the information on the driving state of the driving portion 11*b*, which is sensed by the driving sensor 13*a*.

The danger signal generating portion 13*b* according to one embodiment of the present disclosure may generate danger signals having different information according to the driving state of the driving portion 11*b* sensed by the driving sensor 13*a*, and transmit the danger signals to the control portion.

The danger signal generating portion 13*b* according to one embodiment of the present disclosure may receive information on the rotation of the gear connected to the needle portion 11*a* from the driving sensor 13*a* that senses the rotation of the gear, and when the rotation of the gear is sensed to have a value less than a threshold value according to a predetermined rotation radius, the danger signal generating portion 13*b* may generate a first danger signal related to the rotation of the gear.

When the driving sensor 13*a* according to one embodiment of the present disclosure senses the rotation of the gear, the movement of the needle portion 11*a*, which transmits power through the rotation of the gear, may be indirectly sensed, and when the rotation radius of the gear is sensed to be less than the threshold value, it means that the needle portion 11*a*, which receives the power from the gear, has not been moved by a predetermined length.

When the needle portion 11*a* does not move by the predetermined length, it may mean a state in which the needle portion 11*a* does not pass through the skin of the user H and is blocked by the skin of the user H.

The first danger signal may include information indicating that the rotation radius of the gear does not reach the threshold value, and information indicating that the needle portion 11*a* does not pass through the skin of the user H.

The danger signal generating portion 13*b* according to one embodiment of the present disclosure may receive information on the flow rate of the liquid medicine accommodated in the driving portion 11*b*, specifically the pump, from the driving sensor 13*a* that senses the flow rate of the liquid medicine accommodated in the pump, and sense whether the liquid medicine accommodated in the pump is discharged to the outside by a predetermined amount at a predetermined time interval.

When the flow rate of the liquid medicine, which is flowing into the body of the user H through the tube and the needle portion 11*a* from the pump, is sensed to be below a threshold value according to a predetermined flow rate, a second danger signal related to the flow rate of the liquid medicine may be generated.

When the driving sensor 13*a* according to one embodiment of the present disclosure measures the flow rate of the liquid medicine in the driving portion 11*b*, specifically the pump, the amount of the liquid medicine accommodated in the pump may be indirectly sensed.

When the flow rate of the liquid medicine is sensed to be less than the threshold value, it means that the liquid medicine, such as insulin, is not injected into the body of the user H by a predetermined amount from the pump.

The second danger signal may include information indicating that the flow rate of the liquid medicine injected into the body of the user H does not reach the threshold value, and information indicating that the liquid medicine accommodated in the pump has been consumed and can no longer be supplied.

The danger signal generating portion 13*b* according to one embodiment of the present disclosure may receive the information on the voltage of the battery portion 17 from the driving sensor 13*a*, which senses the voltage of the battery portion 17 that supplies the power source to the liquid medicine injection device, and generate a third danger signal related to the voltage of the battery portion 17 when the voltage of the battery portion 17 is sensed to be below a predetermined threshold value.

When the voltage of the battery portion 17 is sensed to be below the threshold value, it means that the battery portion 17 should be charged. The third danger signal may include information indicating that charging is required because the current voltage of the battery portion 17 is insufficient.

The danger signal generating portion 13*b* according to one embodiment of the present disclosure may receive information on a power source state of the driving portion 11*b* from the driving sensor 13*a* that senses whether the power source is continuously supplied to the driving portion 11*b*, and may generate a fourth danger signal when the power source supplied to the driving portion 11*b* is momentarily cut off.

In the injection portion 10 according to one embodiment of the present disclosure, the driving portion 11*b* should be continuously driven by being supplied with the power source, and when the power source supplied to the driving portion 11*b* is cut off in an unexpected situation, the driving sensor 13*a* may detect and transmit this situation to the danger signal generating portion 13*b* to generate the fourth danger signal.

The control portion according to one embodiment of the present disclosure is electrically connected to the injection portion 10 including the injection body 11, the driving detection portion 13, the battery portion 17, and the first communication portion 19, and the alarm portion 20 including an alarm body 21 and a second communication portion 25, and may control the driving of each of the injection body 11, the driving detection portion 13, and the alarm body 21.

In the present disclosure, the control portion located in the injection portion 10 is defined as the first control portion 15 and the control portion located in the alarm portion 20 is defined as a second control portion 23, and in the following description, the first control portion 15 will be described first, and then the second control portion 23 will be described when describing the alarm portion 20.

Referring to FIG. 10, the first control portion 15 according to one embodiment of the present disclosure is connected to the injection body 11, the driving detection portion 13, the battery portion 17, and the first communication portion 19, and may be provided in the injection portion 10.

The first control portion 15 according to one embodiment of the present disclosure may receive the power source from the battery portion 17 and control the driving of the injection body 11.

The first control portion 15 according to one embodiment of the present disclosure may be connected to the driving detection portion 13, and may receive each of the danger signals generated by the danger signal generating portion 13*b*, specifically, the first danger signal generated on the basis of the information indicating that the rotation radius of the gear does not reach the threshold value and the information indicating that the needle portion 11*a* does not pass through the skin of the user H, the second danger signal generated on the basis of the information indicating that the flow rate of the liquid medicine injected into the body of the user H does not reach the threshold value and the information indicating that the liquid medicine accommodated in the pump has been consumed and can no longer be supplied, the third danger signal generated on the basis of the information indicating that charging is required because the voltage of the battery portion 17 is insufficient, and the fourth danger signal generated on the basis of the information on the case in which the power source supplied to the driving portion 11*b* is momentarily cut off.

In the present disclosure, the first control portion 15 receives the first danger signal, the second danger signal, the third danger signal, and the fourth danger signal from the danger signal generating portion 13*b*, but the present disclosure is not limited thereto, and various modifications are possible, such as, the first control portion 15 may receive the information on the first to fourth danger signals from the driving sensor 13*a*.

The driving sensor 13*a* according to one embodiment of the present disclosure is connected to the battery portion 17 to directly measure the voltage of the battery portion 17, but various modifications are possible, such as the driving sensor 13*a* may receive the information on the battery portion 17 from the control portion to indirectly measure the voltage of the battery portion 17.

The first control portion 15 according to one embodiment of the present disclosure may transmit the danger signals, specifically the first to fourth danger signals, received from the driving detection portion 13, specifically the danger signal generating portion 13*b*, to the first communication portion 19.

The first control portion 15 according to one embodiment of the present disclosure may store data related to the injection portion 10 and data related to the alarm portion 20.

The first control portion 15 may compare the data related to the injection portion 10 with the data related to the alarm portion 20, and generate a request signal on the basis of information on the specific alarm portion 20 so that transmission is possible only from the predetermined injection portion 10 to the predetermined alarm portion 20.

In response to this, the alarm portion 20 to be described below, specifically the second control portion 23 may generate a permission signal, which matches the request signal generated by the first control portion 15, in order to receive only the first to fourth danger signals from the predetermined injection portion 10.

Referring to FIG. 10, the battery portion 17 according to one embodiment of the present disclosure is located in the injection portion 10, and may supply the power source to the injection portion 10. The battery portion 17 may be formed in various types, such as a built-in type, a replaceable type, or the like.

The battery portion 17 according to one embodiment of the present disclosure may be electrically connected to the first control portion 15, the injection body 11, the driving detection portion 13, and the first communication portion 19, and may supply the power source to the first control portion 15, the injection body 11, and the driving detection portion 13.

Referring to FIG. 10, the first communication portion 19 according to one embodiment of the present disclosure is communicatable with the second communication portion 25 located in the alarm portion 20 to be described below. Referring to FIG. 17, the injection portion 10 including the first communication portion 19 according to one embodiment of the present disclosure communicates with the alarm portion 20, in which the second communication portion 25 is installed, in a wireless manner, but the present disclosure is not limited thereto, and various modifications are possible such as in a wired manner.

The first communication portion 19 according to one embodiment of the present disclosure may receive the permission signal and the first to fourth danger signals from the first control portion 15, and transmits the permission signal and the first to fourth danger signals together to the alarm portion 20, specifically the second communication portion 25.

That is, the first communication portion 19 may receive the signals from the first control portion 15, and transmit the request signal and at least one danger signal of the first to fourth danger signals to the second communication portion 25.

Referring to FIGS. 10 and 17, the alarm portion 20 according to one embodiment is a portion that transmits information for detecting an abnormal symptom of a driving state of the injection portion 10, and may include the alarm body 21, the second control portion 23, the second communication portion 25, a band portion 29.

When an abnormal symptom occurs in the driving state of the injection body 11 while the alarm body 21 according to one embodiment of the present disclosure is in contact with the user H, the alarm body 21 may transmit information on this to the user H so that the user H can detect it.

The alarm body 21 according to one embodiment of the present disclosure may be electrically connected to the second control portion 23 and the second communication portion 25, which will be described below. Although not shown in the drawings, the alarm body 21 may be connected to a separate battery and may receive a power source from the battery.

Referring to FIG. 17, the alarm body 21 according to one embodiment of the present disclosure may be installed in an alarm housing (not designated by a reference numeral), which forms an exterior of the alarm portion 20, together with the second control portion 23, the second communication portion 25, and the battery. The alarm housing may be connected to the band portion 29 to be described below.

The alarm body 21 according to one embodiment of the present disclosure may include a stimulation transmission portion 21*a* and a display portion 21*b*. The stimulation transmission portion 21*a* according to one embodiment of the present disclosure receives an electrical signal from the second control portion 23 and applies a stimulation to the user H, and may include an electrode portion 21*a*1 and a stimulation signal generating portion 21*a*3.

The electrode portion 21*a*1 according to one embodiment of the present disclosure is capable of being in contact with the user H, and may be disposed to be in direct contact with the skin of the user H. The electrode portion 21*a*1 may be located on a bottom surface of the alarm housing facing the skin of the user H such as the wrist.

The electrode portion 21*a*1 according to one embodiment of the present disclosure may receive a stimulation signal from the stimulation signal generating portion 21*a*3, and transmit an electrical stimulation to the muscle of the user H through the skin of the user H which is in contact with the electrode portion 21*a*1. In the present disclosure, the electrical stimulation may be formed of a low-frequency electrical stimulation.

Accordingly, when the electrical stimulation is transmitted from the electrode portion 21*a*1 to the skin of the user H, only the user H himself/herself can recognize that the abnormal symptom has occurred in the driving state of the injection portion 10 without exposing the fact that the abnormal symptom has occurred in the driving state of the injection portion 10.

Accordingly, the privacy of the user H is not exposed to the outside as compared to the method in which the abnormal symptom is notified to the user H aurally, such as by sound.

Referring to FIG. 14, the stimulation signal generating portion 21*a*3 according to one embodiment of the present disclosure generates the stimulation signal, and may be connected to the second control portion 23. In addition, the stimulation signal generating portion 21*a*3 may be connected to the electrode portion 21*a*1, and may transmit the stimulation signal to the electrode portion 21*a*1.

The stimulation signal generating portion 21*a*3 according to one embodiment of the present disclosure may generate one or more stimulation signals. The one or more stimulation signals may be formed by varying a stimulation cycle of the stimulation that is transmitted to the muscle of the user H.

In the present disclosure, the term "stimulation cycle" refers to varying the rhythm of a period in which the stimulation becomes zero (0) when the electrical stimulation is transmitted through the skin, such as the wrist of the user H.

Specifically, the stimulation signal generating portion 21*a*3 according to one embodiment of the present disclosure may generate stimulation signals respectively corresponding to one or more danger signals, which are received from the second control portion 23 through the second communication portion 25, specifically, the first danger signal generated on the basis of the information indicating that the rotation radius of the gear does not reach the threshold value and the information indicating that the needle portion 11*a* does not pass through the skin of the user H, the second danger signal generated on the basis of the information indicating that the flow rate of the liquid medicine injected into the body of the user H does not reach the threshold value and the information indicating that the liquid medicine accommodated in the pump has been consumed and can no longer be supplied, the third danger signal generated on the basis of the information indicating that charging is required because the voltage of the battery portion 17 is insufficient, and the fourth danger signal generated on the basis of the information on the case in which the power source supplied to the driving portion 11*b* is momentarily cut off.

That is, the stimulation signal generating portion 21*a*3 may generate a first stimulation signal corresponding to the first danger signal indicating that the rotation radius of the driving portion 11*b*, specifically the gear, does not reach the threshold value, a second stimulation signal corresponding to the second danger signal indicating that the liquid medicine accommodated in the pump has been consumed and thus the liquid medicine can no longer be supplied to the body of the user H, a third stimulation signal corresponding to the third danger signal indicating that the voltage of the battery portion 17 is insufficient, and a fourth stimulation signal corresponding to the fourth danger signal related to the momentarily cutting off the power source supplied to the driving portion 11*b*, that is, a reset.

The first to fourth stimulation signals may be transmitted to the second control portion 23, and the second control portion 23 may control the cycle of the stimulation signal transmitted to the user H so that the user H can distinguish a specific danger signal from among the first to fourth danger signals respectively corresponding to the first to fourth stimulation signals when the first to fourth stimulation signals are transmitted to the user H through the electrode portion 21*a*1.

Referring to FIGS. 13 and 17, the display portion 21*b* according to one embodiment of the present disclosure is connected to the second control portion 23, and may receive information on the driving state of the injection portion 10 from the second control portion 23.

The display portion 21*b* according to one embodiment of the present disclosure may visually transmit the information on the driving state of the injection portion 10 to the user H. Although not shown in the drawings, the user H may turn the display portion 21*b* on/off through a separate operation portion.

Accordingly, the user H may receive the first to fourth stimulation signals respectively corresponding to the first to fourth danger signals related to the abnormal symptoms of the driving state of the injection portion 10 from the stimulation transmission portion 21*a*, specifically the electrode portion 21*a*1.

Referring to FIGS. 10, 13, and 14, the second control portion 23 according to one embodiment of the present disclosure is electrically connected to the alarm body 21, and is located in the alarm portion 20. Specifically, the second control portion 23 may be electrically connected to the stimulation transmission portion 21*a* and the display portion 21*b*. In addition, the second control portion 23 may be connected to the second communication portion 25.

The second control portion 23 may receive the request signal and at least one danger signal of the first to fourth danger signals from the second communication portion 25. Like the first control portion 15, data related to the injection portion 10 and data related to the alarm portion 20 may be stored in the second control portion 23.

The second control portion 23 may compare the data related to the injection portion 10 with the data related to the alarm portion 20 and generate a permission signal on the basis of the information on the specific injection portion 10 so that the danger signal may be received only from the predetermined injection portion 10.

Accordingly, the second control portion 23 may receive the first to fourth danger signals from the predetermined injection portion 10.

Referring to FIG. 10, the second communication portion 25 according to one embodiment of the present disclosure is communicatable with the first communication portion 19 located in the injection portion 10. Referring to FIG. 17, the second communication portion 25 according to one embodiment of the present disclosure communicates with the first communication portion 19 in a wireless manner, but the present disclosure is not limited thereto, and various modifications are possible such as in a wired manner.

The second communication portion 25 according to one embodiment of the present disclosure may receive the permission signal and the first to fourth danger signals from the first communication portion 19, and transmit the permission signal and the first to fourth danger signals together to the second control portion 23.

That is, the second communication portion 25 may receive the signals from the first communication portion 19, and transmit the request signal and at least one danger signal of the first to fourth danger signals to the second control portion 23.

The second control portion 23 may compare the request signal received from the second communication portion 25 with the permission signal, and transmit the first to fourth danger signals to the stimulation signal generating portion 21*a*3 when the request signal and the permission signal match each other, that is, correspond to each other.

Referring to FIG. 17, the band portion 29 according to one embodiment of the present disclosure is coupled to the alarm housing, and may maintain the state in which the alarm body 21, specifically, the stimulation transmission portion 21*a* is in contact with the user H.

The band portion 29 according to one embodiment of the present disclosure may be formed to be worn around the wrist of the user H.

The operation principle and effect of the above-described liquid medicine injection device 1 will be described.

Referring to FIGS. 10 to 17, the liquid medicine injection device 1 according to one embodiment of the present disclosure may include the injection portion 10 and the alarm portion 20.

Referring to FIG. 17, the injection portion 10 may be attached to the human body, such as the abdomen or waist of a user H, in the form of a patch for a predetermined period of time. The alarm portion 20 is separated from the injection portion 10, and may be worn on the wrist of the user H.

Referring to FIGS. 10 and 17, the alarm portion 20 is communicatable with the injection portion 10, and may receive information for detecting an abnormal symptom of a driving state of the injection portion 10 and apply a stimulation in a state of being in contact with the user H.

The alarm portion 20 according to one embodiment of the present disclosure may transmit an electrical stimulation to the muscle of the user H through the skin of the user H which is in contact the alarm portion 20.

Referring to FIGS. 10 to 12, the injection portion 10 according to one embodiment of the present disclosure may include the injection body 11, the driving detection portion 13, the first control portion 15, the battery portion 17, and the first communication portion 19.

The driving detection portion 13 may detect information on a driving state of the injection body 11 that injects a liquid medicine into the body of the user H.

Referring to FIGS. 11 and 12, the injection body 11 may include the needle portion 11*a* and the driving portion 11*b*, and the driving detection portion 13 may include the driving sensor 13*a* and the danger signal generating portion 13*b*.

Referring to FIG. 15, in sensing a driving state of the driving portion 11*b* (S10), the driving detection portion 13, specifically the driving sensor 13*a*, may detect information on the driving state of the driving portion 11*b*.

When the driving sensor 13*a* senses and detects the information on the driving state of the driving portion 11*b*, the sensed information is transmitted to the danger signal generating portion 13*b* (S20).

The danger signal generating portion 13*b* has been stored a threshold value related to the driving state of the driving portion 11*b*, and compares the information on the driving state of the driving portion 11*b* received from the driving sensor 13*a*, that is, the sensed value, with the threshold value (S30).

When the sensed value reaches the threshold value, the sensing of the driving state of the driving portion 11*b* by the driving sensor 13*a* (S10) is continuously repeated. On the other hand, when the sensed value does not reach the threshold value, the danger signal generating portion 13*b* generates a danger signal (S40).

Specifically, the driving sensor 13*a* may be electrically connected to the driving portion 11*b*, and may sense the driving state of the driving portion 11*b*. Specifically, the driving sensor 13*a* may sense the rotation of the gear that moves the needle portion 11*a*, and transmits information on the rotation of the gear to the danger signal generating portion 13*b*.

The danger signal generating portion 13*b* may generate a first danger signal related to the rotation of the gear when the information on the rotation of the driving portion 11*b*, specifically the gear, is received from the driving sensor 13*a* and sensed to be below a threshold value according to a predetermined rotation radius.

When the rotation radius of the gear reaches the threshold value, the driving sensor 13*a* does not transmit an electrical signal to the danger signal generating portion 13*b*, and continuously senses a rotation state of the driving portion 11*b*, specifically the gear.

The driving sensor 13*a* may measure a flow rate of the liquid medicine in the pump by receiving information on the flow rate of the liquid medicine accommodated in the driving portion 11*b*, specifically the pump, and sensing whether the liquid medicine accommodated in the pump is discharged to the outside by a predetermined amount at a predetermined time interval.

The danger signal generating portion 13*b* may generate a second danger signal related to an insufficient flow rate of the liquid medicine when the flow rate of the liquid medicine flowing into the body of the user H through the tube in the driving portion 11*b*, specifically the pump, and the needle portion 11*a* is sensed to be below a threshold value according to a predetermined flow rate by the driving sensor 13*a*. Information on the insufficient flow rate of the liquid medicine may mean a lack in the amount of the liquid medicine accommodated in the pump.

The driving sensor 13*a* may measure a voltage of the battery portion 17 by receiving information on the voltage of the battery portion 17 that supplies a power source to the driving portion 11*b* and sensing the voltage of the battery portion 17.

The danger signal generating portion 13*b* may generate a third danger signal related to the voltage of the battery portion 17 when the voltage of the battery portion 17 that supplies the power source to the driving portion 11*b*, specifically the driving portion 11*b*, is sensed to be below a predetermined threshold value by the driving sensor 13*a*.

The information on the voltage of the battery portion 17 may include information indicating that charging is required because the current voltage of the battery portion 17 is insufficient.

The driving sensor 13*a* may receive information on a power source state of the driving portion 11*b* and sense whether the power source supplied to the driving portion 11*b* is momentarily cut off. In the injection portion 10, the state in which the driving portion 11*b* is continuously driven by being supplied with the power source should be maintained, and a case in which the power source supplied to the driving portion 11*b* is cut off in an unexpected situation may be detected.

The danger signal generating portion 13*b* may receive information on whether the power source is continuously supplied to the driving portion 11*b* from the driving sensor 13*a*, and may generate a fourth danger signal when the voltage in the power source supplied to the driving portion 11*b* momentarily becomes zero or sensed to be less than a predetermined threshold value by the driving sensor 13*a*.

After the generating of the danger signal by the danger signal generating portion 13*b* (S40), transmitting and receiving the danger signal (S50) may be included.

In the transmitting and receiving of the danger signal (S50), the first to fourth danger signals generated for each sensing situation of the driving sensor 13*a* may be transmitted to the first control portion 15, as described above. The first control portion 15 may store information on the injection portion 10, and may generate a request signal on the basis of the information on the injection portion 10.

The first control portion 15 receives at least one of the first to fourth danger signals related to a driving state of the injection body 11, specifically, an abnormal symptom of the driving state of the driving portion 11*b*, and transmits the first to fourth danger signals to the first communication portion 19 together with the request signal.

The first communication portion 19 may transmit the request signal and at least one of the first to fourth danger signals to the second communication portion 25 through wireless communication. In the present disclosure, the first communication portion 19 and the second communication portion 25 are wirelessly connected and transmit and receive signals, but the present disclosure is not limited thereto, and various modifications are possible such as the signals are transmitted and received by being connected in a wired manner.

Referring to FIGS. 15 and 16, the transmitting and receiving of the danger signal (S50) may include transmitting and receiving the danger signal and the request signal (S51), determining whether the request signal and a permission signal match each other (S52), and transmitting the danger signal to the stimulation signal generating portion 21*a*3 (S53).

In the transmitting and receiving of the danger signal and the request signal (S51), the second communication portion 25 may receive the request signal and the danger signal from the first communication portion 19 and transmit the request signal and the danger signal to the second control portion 23.

Information on the injection portion 10 and information on the alarm portion 20 may be transmitted to the second control portion 23, and the second control portion 23 may generate the permission signal on the basis of the information on the alarm portion 20.

When the request signal and the danger signal are transmitted to the second control portion 23, the second control portion 23 may determine whether the request signal, which is generated from the injection portion 10 and for requesting access to the predetermined alarm portion 20, matches the permission signal that is generated from the alarm portion 20 and for permitting the access only to the predetermined injection portion 10.

The second control portion 23 may determine whether the injection portion 10 is allowed to be connected to the predetermined alarm portion 20 on the basis of the information on the injection portion 10 and the alarm portion 20 respectively stored in the request signal and the permission signal.

By determining whether the request signal and the permission signal match, only the predetermined alarm portion 20 may detect and transmit the abnormal symptom of the driving state of the driving portion 11*b* of the predetermined injection portion 10, thereby improving alarm accuracy.

When the request signal matches the permission signal in the determining of whether the request signal and the permission signal match (S52), the second control portion 23 may transmit the danger signal to the stimulation signal generating portion 21*a*3.

The stimulation signal generating portion 21*a*3 may generate a stimulation signal corresponding to each of one or more danger signals received from the second control portion 23 and the above-described first to fourth danger signals.

That is, the stimulation signal generating portion 21*a*3 may generate a first stimulation signal corresponding to the first danger signal indicating that the rotation radius of the driving portion 11*b*, specifically the gear, does not reach the threshold value, a second stimulation signal corresponding to the second danger signal indicating that the liquid medicine accommodated in the pump has been consumed and thus the liquid medicine can no longer be supplied to the body of the user H, a third stimulation signal corresponding to the third danger signal indicating that the voltage of the battery portion 17 is insufficient, and a fourth stimulation signal corresponding to the fourth danger signal related to the momentarily cutting off the power source supplied to the driving portion 11*b*, that is, a reset.

The first to fourth stimulation signals may be transmitted to the second control portion 23, and the second control portion 23 may control the cycle of the stimulation signal transmitted to the user H so that the user H can distinguish the first to fourth danger signals respectively corresponding to the first to fourth stimulation signals when the first to fourth stimulation signals are transmitted to the user H through the electrode portion 21*a*1.

The second control portion 23 may transmit the first to fourth stimulation signals to the electrode portion 21*a*1 and transmit a stimulation to the user H through the electrode portion 21*a*1 (S70).

Specifically, the electrode portion 21*a*1 may receive the first to fourth stimulation signals from the stimulation signal generating portion 21*a*3, and transmit an electrical stimulation to the muscle of the user H through the skin of the user H which is in contact the electrode portion 21*a*1.

The electrode portion 21*a*1 is located in the alarm portion 20 while being in contact with the skin of the user H such as the wrist, and is not exposed to the outside as the user H wears the alarm portion 20.

Accordingly, the third party except for the user H may not recognize the stimulation that is transmitted to the user H when the abnormal symptom of the driving state of the injection portion 10 is detected, and only the user H may receive the electrical stimulation by being in contact with the electrode portion 21*a*1.

In addition, the user H may distinguish the type of the current abnormal symptom of the driving state of the injection body 11 only by a tactile sensation by receiving the stimulation signals that form different stimulation cycles to correspond to the danger signal for different abnormal symptoms of the driving state of the injection body 11 through the electrode portion 21*a*1.

The particular implementations shown and described herein are illustrative examples of the embodiments and are not intended to otherwise limit the scope of the embodiments in any way. For the sake of brevity, conventional electronics, control systems, software development and other functional aspects of the systems may not be described in detail. Further, the connecting lines or connectors shown in the drawings are intended to represent example functional relationships and/or physical or logical couplings between the various elements. It should be noted that many alternative or additional functional relationships, physical connections, or logical connections may be present in a practical device. In addition, no item or element is essential to the practice of the present disclosure unless the element is specifically described as "essential" or "critical".

Accordingly, it should be noted that the spirit of the present disclosure is not limited to the embodiments described above, and not only the claims to be described later, but also all ranges equivalent to or equivalently changed from the claims fall within the scope of the spirit of the present disclosure.

INDUSTRIAL APPLICABILITY

According to the present disclosure, a liquid medicine injection device is provided. In addition, the embodiments of the present disclosure may be applied to a liquid medicine injection device capable of injecting a liquid medicine into the body of a user, and the like.

The invention claimed is:

1. A liquid medicine injection device comprising:

a patch portion to which a sensor portion configured to measure blood glucose is detachably attached and in which an injection portion configured to inject a liquid medicine into a body of a user is installed; and a stamping portion on which the patch portion is mounted and including a first needle connectable to the sensor portion, wherein the stamping portion transmits power to the patch portion so that the first needle and a second needle, which is connected to the injection portion, are together inserted into a skin of the user, wherein the stamping portion comprises:

a first body allowed to be gripped by the user;

a second body that is relatively movable inside the first body; and a patch holder portion that is connected to the second body, disposed to be spaced apart from the first body by a predetermined separation distance, and in which the patch portion is mounted, wherein the stamping portion further comprises a power transmission portion configured to connect the first body and the patch holder portion and transmit power to the injection portion to separate the second needle connected to the injection portion from the skin of the user, wherein the power transmission portion rotates in a clockwise direction or a counterclockwise direction and transmits rotational power to the injection portion, wherein the power transmission portion comprises:

a power transmission shaft formed to extend in a longitudinal direction and configured to rotate about a longitudinal central axis in the clockwise direction or the counterclockwise direction; and a shaft holder portion that is connected to the power transmission shaft and movable on the power transmission shaft, wherein the power transmission shaft comprises a rotation guide groove formed therein, the rotation guide groove including two or more linear paths formed parallel to each other and bent connection portions connecting between the two or more linear paths, wherein the shaft holder portion comprises a guide body protruding toward the power transmission shaft, and wherein the guide body is seated in the rotation guide groove.

2. The liquid medicine injection device of claim 1, wherein the injection portion comprises:

an injection cover connected to the power transmission portion;

an injection housing coupled to the injection cover and having a hollow interior;

a tube portion installed in the injection housing and having a hollow interior; and a second needle holder portion which is movably disposed inside the injection housing and in which the second needle insertable into the tube portion is installed.

3. The liquid medicine injection device of claim 2, wherein the injection housing and the second needle holder portion share a rotation central axis and are relatively rotatable with respect to each other.

4. The liquid medicine injection device of claim 2, wherein the injection portion further comprises a sealing member coupled along an outer circumferential surface of the injection cover.

5. The liquid medicine injection device of claim 4, wherein the sealing member is formed in a ring shape.

6. The liquid medicine injection device of claim 1, wherein a movement control portion, disposed between the shaft holder portion and the second body and configured to control a movement of the shaft holder portion, is formed in the patch holder portion.

7. The liquid medicine injection device of claim 1, further comprising a first needle holder portion in which the first needle is installed, and which is relatively movable with respect to the patch holder portion.

8. The liquid medicine injection device of claim 7, wherein the first needle holder portion comprises:

a first needle holder body to which the first needle is positionally fixed; and an elastic member coupled to each of the first needle holder body and the patch holder portion and configured to elastically support the first needle holder body in a direction away from the patch holder portion.

9. The liquid medicine injection device of claim 8, wherein a movement control portion, disposed between the first needle holder portion and the second body and configured to control a movement of the first needle holder portion, is formed in the patch holder portion.

10. The liquid medicine injection device of claim 1, wherein a sensor mounting groove on which the sensor portion is mountable is formed in the shape of a groove in the patch portion, and the liquid medicine injection device further comprises a sensor mounting portion that is couplable to the stamping portion, and has one surface facing the patch portion in which the sensor mounting groove is formed and on which the sensor portion is disposed to protrude.

11. The liquid medicine injection device of claim 10, wherein the sensor portion comprises:

a sensor module including a sensor needle disposed inside the first needle; and a sensor cover coupled to the sensor module and configured to cover the sensor module.

* * * * *